United States Patent
Ishihara et al.

(10) Patent No.: US 9,018,394 B2
(45) Date of Patent: Apr. 28, 2015

(54) METHOD FOR PRODUCING AROMATIC COMPOUND HAVING RING STRUCTURE THAT INCLUDES NITROGEN ATOM OR OXYGEN ATOM

(75) Inventors: Kazuaki Ishihara, Nagoya (JP); Uyanik Muhammet, Nagoya (JP)

(73) Assignee: National University Corporation Nagoya University, Nagoya-shi (JP)

( * ) Notice: Subject to any disclaimer, the term of this patent is extended or adjusted under 35 U.S.C. 154(b) by 0 days.

(21) Appl. No.: 13/982,424

(22) PCT Filed: Feb. 2, 2012

(86) PCT No.: PCT/JP2012/052424
§ 371 (c)(1),
(2), (4) Date: Aug. 30, 2013

(87) PCT Pub. No.: WO2012/111449
PCT Pub. Date: Aug. 23, 2012

(65) Prior Publication Data
US 2013/0338371 A1    Dec. 19, 2013

(30) Foreign Application Priority Data
Feb. 18, 2011    (JP) ................ 2011-033808

(51) Int. Cl.
C07D 403/06 (2006.01)
C07D 209/12 (2006.01)
C07D 209/42 (2006.01)
C07D 307/94 (2006.01)

(52) U.S. Cl.
CPC ............ C07D 403/06 (2013.01); C07D 209/12 (2013.01); C07D 307/94 (2013.01); C07D 209/42 (2013.01)

(58) Field of Classification Search
CPC ... C07D 403/06; C07D 209/42; C07D 307/94
USPC ........................ 548/312.1, 493, 492; 549/265
See application file for complete search history.

(56) References Cited

FOREIGN PATENT DOCUMENTS

JP        2009-149564 A       7/2009
WO     WO 2011052388 A1 *  5/2011

OTHER PUBLICATIONS

Uyanik et al. "Hypervalent iodine-catalyzed oxylactonization of ketocarboxylic acids to ketolactones" Bioorg. Med. Chem. Lett. 2009, 19, 3848-3851.*

International Search Report issued Mar. 13, 2012 in PCT/JP2012/052424.
Jin-Qiang Liu et al., "A Facile Chiral Pool Synthesis of (S)-6-Nitroindoline-2-carboxylic Acid from L-Phenylalanine", Synthesis 2010, No. 3, pp. 403-406.
Jeffrey N. Johnston et al., "Free Radical-Mediated Aryl Amination and Its Use in a Convergent [3+2] Strategy for Enantioselective Indoline α-Amino Acid Synthesis", J. Am. Chem. Soc. 2003, 125, pp. 163-168.
Wanbin Zhang et al., "Pd-catalyzed Asymmetric aza-Wacker-type Cyclization Reaction of Olefinic Tosylamides", Tetrahedron Letters 51, 2010, pp. 5124-5126.
Hirofumi Yamamoto et al., "Hg(OTf)$_2$-Binaphane-Catalyzed Enantioselective Anilino Sulfonamide Allyl Alcohol Cyclization", Chem. Eur. J. 2010, 16, pp. 11271-11274.
Rich G. Carter et al., "Improved Protocol for Asymmetric, Intramolecular Heteroatom Michael Addition Using Organocatalysis: Enantioselective Syntheses of Homoproline, Pelletierine, and Homopipecolic Acid", J. Org. Chem. 2008, 73, pp. 5155-5158.
Yasuyuki Kita et al., "A Chiral Hypervalent Iodine (III) Reagent for Enantioselective Dearomatization of Phenols", Angew. Chem. Int. Ed. 47 (2008), pp. 3787-3790.
Kazuaki Ishihara et al., "Enantioselective Kita Oxidative Spirolactonization Catalyzed by in Situ Generated Chiral Hypervalent Iodine (III) Species", Angew. Chem. Int. Ed. 49 (2010), pp. 2175-2177.
Piero Della Croce et al., "2-(Tosylamino)Benzyltrimethylammonium Halides As Precursors of 2-Substituted Indoles", Heterocycles, vol. 43, No. 11, 1996, pp. 2397-2407.
Muhammet Uyanik et al., "Chiral Hypervalent Iodine-catalyzed Enantioselective Oxidative Kita Spirolactonization of 1-naphthol Derivatives and One-pot Diastereo-selective Oxidation to Epoxyspirolactones", Tetrahedron, vol. 66, No. 31, 2010, pp. 5841-5851.

* cited by examiner

*Primary Examiner* — Joseph Kosack
*Assistant Examiner* — Amanda L Aguirre
(74) *Attorney, Agent, or Firm* — Oblon, McClelland, Maier & Neustadt, L.L.P.

(57) ABSTRACT

The invention is a method for efficiently producing an aromatic compound by an intramolecular cyclization reaction, the aromatic compound having a ring structure that includes a nitrogen atom or oxygen atom. An aromatic compound composed of tert-butyl-2-(3-oxo-3-phenylpropyl)phenyl carbamate or another aniline derivative or the like, or an aromatic compound composed of 3-(1-hydroxynaphthalene-2-yl)propionic acid or another naphthol derivative or the like is made to react in a system to which an oxidizing agent and a quaternary ammonium salt represented by general formula (1) are fed. In the formula, X is an iodine atom; and $R^1, R^2, R^3$ and $R^4$ are each independently a $C_{1-30}$ hydrocarbon group in which some hydrogen atoms are optionally substituted with halogen atoms, or $R^1$ and $R^2$ may be combine to form a divalent organic group bonded to a nitrogen atom, and $R^3$ and $R^4$ may combine to form a divalent organic group bonded to a nitrogen atom.

12 Claims, No Drawings

METHOD FOR PRODUCING AROMATIC COMPOUND HAVING RING STRUCTURE THAT INCLUDES NITROGEN ATOM OR OXYGEN ATOM

TECHNICAL FIELD

The present invention relates to a method for efficiently producing an aromatic compound having a ring structure that includes a nitrogen atom or an oxygen atom via an intramolecular cyclization reaction. The invention can be used for a method for producing a physiologically active substance, a drug, an agricultural chemical, a cosmetic preparation, or the like.

BACKGROUND ART

A 2-acylindoline, a spirolactone, and the like have been known as an intermediate or the like used when producing a physiologically active substance, a drug, an agricultural chemical, a cosmetic preparation, or the like. An optically active compound may be used from the viewpoint of the effects of the end product and the like.

A method for producing an indoline derivative is disclosed in, for example, Non-patent Documents 1 to 5.

Non-patent Document 1 discloses a method that subjects an optically active amino acid derivative to an intramolecular coupling (amination) reaction using a transition metal catalyst.

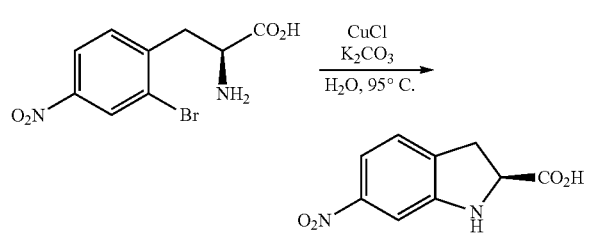

Non-patent Document 2 discloses a method that subjects a glycine ester to asymmetric alkylation using a chiral phase transfer catalyst, and then effects an intramolecular free radical cyclization reaction.

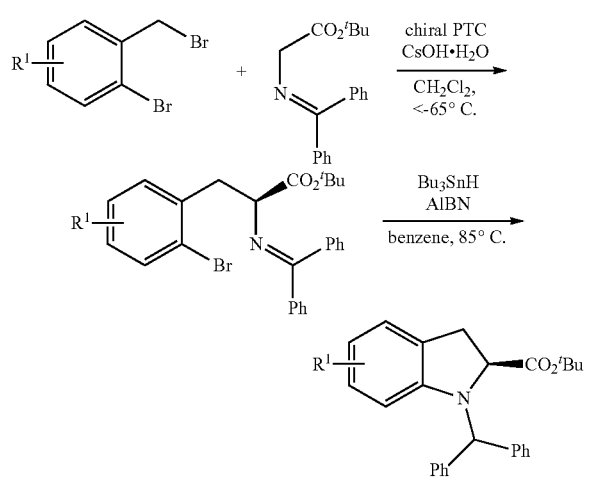

Non-patent Document 3 discloses a method that subjects an alkenyl N-tosylanilide to an aza-Wacker oxidative cyclization reaction using a chiral palladium complex as a catalyst.

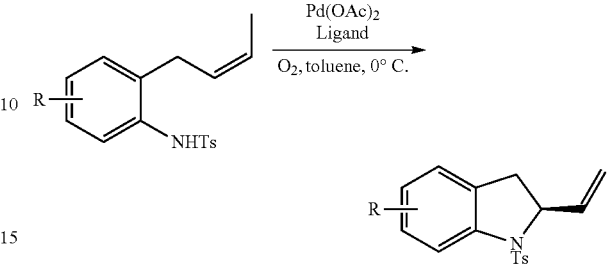

Non-patent Document 4 discloses a method that subjects N-sulfonylanilide allyl alcohol to a dehydration cyclization reaction using a chiral mercury complex as a catalyst.

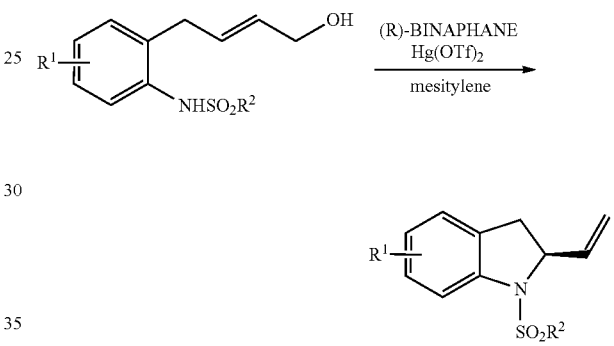

Non-patent Document 5 discloses a method that subjects an anilide unsaturated aldehyde to an aza-Michael reaction using an optically active amine as a catalyst.

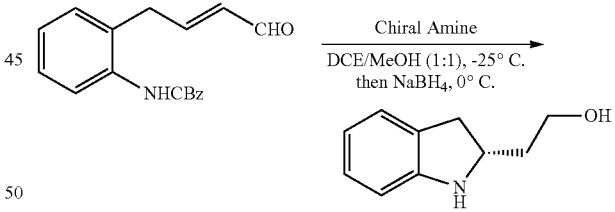

A method for producing a spirolactone is disclosed in, for example, Patent Document 1, Non-patent Document 6 and the like.

Patent Document 1 and Non-patent Document 6 disclose a method that produces an optically active spirolactone compound in a solvent (e.g., chloroform) using a hypervalent iodine compound having a chiral spirobiindane skeleton as an oxidizing agent. Patent Document 1 and Non-patent Document 6 also disclose a method that produces an optically active spirolactone compound by subjecting 1-naphthol to a catalytic enantioselective aromatization oxidation reaction in the presence of a hypervalent iodine compound prepared from a hypervalent iodine compound precursor and meta-chloroperbenzoic acid (m-CPBA).

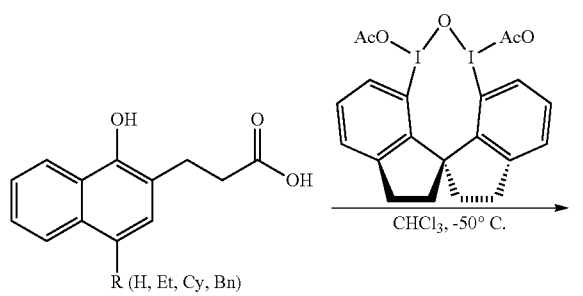

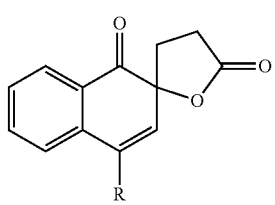

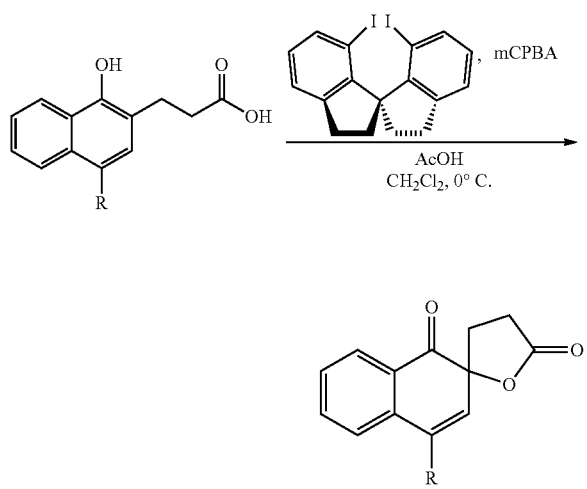

Non-patent Document 7 discloses a method that produces an optically active spirolactone compound by subjecting 1-naphthol to a catalytic enantioselective aromatization oxidation reaction in the presence of a hypervalent iodine compound prepared from an optically active iodine compound (obtained from 2,6-dihydroxyiodobenzene using lactic acid as a chiral source) and meta-chloroperbenzoic acid (m-CPBA).

RELATED-ART DOCUMENT

Patent Document

Patent Document 1: JP-A 2009-149564

Non-Patent Document

Non-patent Document 1: Qian, et al., Synthesis (2010) 403
Non-patent Document 2: Johnston, et al., J. Am. Chem. Soc. 125 (2003) 163
Non-patent Document 3: Zhang, et al., Tetrahedron Lett. 51 (2010) 5124
Non-patent Document 4: Yamamoto, Nishizawa, et al., Chem. Eur. J. 16 (2010) 11271
Non-patent Document 5: Carter, et al., J. Org. Chem. 73 (2008) 5155
Non-patent Document 6: Kita, et al., Angew. Chem. Int. Ed. 47 (2008) 3787
Non-patent Document 7: Uyanik, Ishihara, et al., Angew. Chem. Int. Ed. 49 (2010) 2175

SUMMARY OF THE INVENTION

Technical Problem

The related-art 2-acylindoline production methods have problems in that a catalyst having a metal element is used, multi-stage reactions are required, the chemical yield is insufficient, and the substrate generality is insufficient, for example.

The related-art spirolactone production methods have problems in that a chlorine-based solvent (for which avoidance of use or a reduction in usage amount has been desired from the viewpoint of the effects on human body and the environmental impact) is used as a reaction solvent, and it may be difficult to separate a decomposition product of the oxidizing agent from the reaction system after completion of the reaction, for example.

An object of the present invention is to provide a method that efficiently produces an aromatic compound having a ring structure that includes a nitrogen atom or an oxygen atom by promoting an intramolecular cyclization reaction in a reaction system that is supplied with a quaternary ammonium salt and an oxidizing agent.

Another object of the present invention is to provide a method that produces an aromatic compound with high enantioselectivity.

Solution to Problem

The present inventors conducted extensive studies in order to implement a method that efficiently produces an aromatic

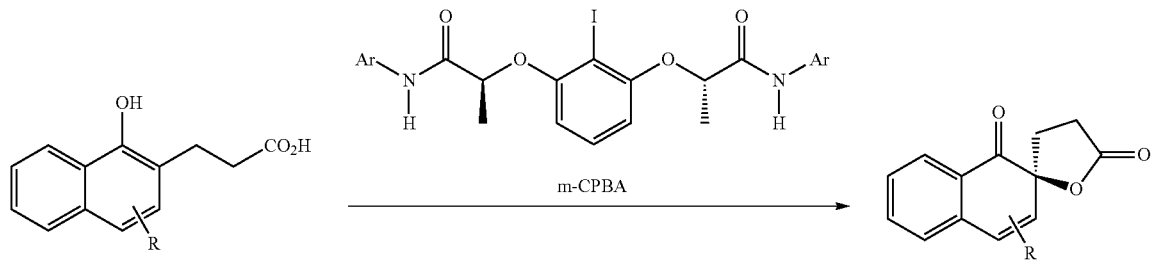

compound having a ring structure that includes a nitrogen atom or an oxygen atom. As a result, the inventors completed the invention.

The present invention is as follows.
1. A method comprising reacting a substrate in a system that is supplied with a quaternary ammonium salt represented by a general formula (1) and an oxidizing agent to produce a compound having a ring structure, the substrate is an aromatic compound in which an amino group represented by —NHR$^{11}$ (wherein R$^{11}$ is a hydrogen atom, a tert-butoxycarbonyl group, a benzyloxycarbonyl group, a 2,2,2-trichloroethoxycarbonyl group, or a methanesulfonyl group) and —R$^{13}$—CHR$^{15}$—C(O)—R$^{17}$ (wherein R$^{13}$ is a divalent hydrocarbon group in which some of hydrogen atoms may be substituted with a substituent, R$^{15}$ is a hydrogen atom or a linear, branched or cyclic hydrocarbon group having 1 to 20 carbon atoms in which some of hydrogen atoms may be substituted with a halogen atom, and R$^{17}$ is a heteroaryl group having 3 to 20 carbon atoms, a derivative group thereof, or a linear, branched or cyclic hydrocarbon group having 1 to 20 carbon atoms in which some of hydrogen atoms may be substituted with a halogen atom) are respectively bonded to two adjacent carbon atoms that form a benzene ring, or an aromatic compound in which a hydroxyl group and a carboxyl group are respectively bonded to carbon atoms that form a naphthalene ring and are situated at position 1 or 2, the carboxyl group is bonded via a chain hydrocarbon group in which some of hydrogen atoms may be substituted with a halogen atom, the ring structure including a nitrogen atom derived from the amino group or an oxygen atom derived from the carboxyl group,

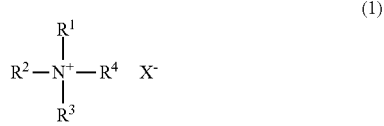

(1)

wherein X is an iodine atom, and R$^1$, R$^2$, R$^3$ and R$^4$ are independently a hydrocarbon group having 1 to 30 carbon atoms in which some of hydrogen atoms may be substituted with a halogen atom, provided that R$^1$ and R$^2$ may be bonded to each other to form a divalent organic group that is bonded to the nitrogen atom, and R$^3$ and R$^4$ may be bonded to each other to form a divalent organic group that is bonded to the nitrogen atom.
2. The method according to 1 above, wherein the quaternary ammonium salt is an N-spiro quaternary ammonium salt represented by a general formula (2),

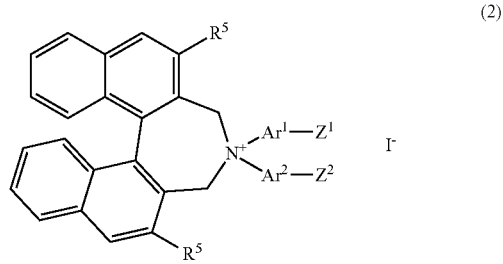

(2)

wherein R$^5$ is a group selected from the group consisting of a hydrogen atom, a linear, branched or cyclic alkyl group having 1 to 6 carbon atoms in which some of hydrogen atoms may be substituted with a halogen atom, a linear, branched or cyclic alkenyl group having 2 to 6 carbon atoms in which some of hydrogen atoms may be substituted with a halogen atom, a linear, branched or cyclic alkynyl group having 2 to 6 carbon atoms in which some of hydrogen atoms may be substituted with a halogen atom, an aralkyl group in which some of hydrogen atoms may be substituted with an alkyl group having 1 to 4 carbon atoms in which some of hydrogen atoms may be substituted with a halogen atom, an alkoxy group having 1 to 3 carbon atoms in which some of hydrogen atoms may be substituted with a halogen atom, or a halogen atom, a heteroaralkyl group in which some of hydrogen atoms may be substituted with an alkyl group having 1 to 4 carbon atoms in which some of hydrogen atoms may be substituted with a halogen atom, an alkoxy group having 1 to 3 carbon atoms in which some of hydrogen atoms may be substituted with a halogen atom, or a halogen atom, an aryl group in which some of hydrogen atoms may be substituted with an alkyl group having 1 to 4 carbon atoms in which some of hydrogen atoms may be substituted with a halogen atom, an alkoxy group having 1 to 3 carbon atoms in which some of hydrogen atoms may be substituted with a halogen atom, or a halogen atom, an aryl group in which some of hydrogen atoms are substituted with an aryl group that may be substituted with an alkyl group having 1 to 4 carbon atoms in which some of hydrogen atoms may be substituted with a halogen atom, a heteroaryl group in which some of hydrogen atoms may be substituted with an alkyl group having 1 to 4 carbon atoms in which some of hydrogen atoms may be substituted with a halogen atom, an alkoxy group having 1 to 3 carbon atoms in which some of hydrogen atoms may be substituted with a halogen atom, or a halogen atom, a ($C_{1-3}$ alkoxy) carbonyl group, an N—($C_{1-4}$ alkyl)carbonyl group, a carbamoyl group, an N—($C_{1-4}$ alkyl)carbamoyl group, and an N,N-di($C_{1-4}$ alkyl)carbamoyl group (wherein the $C_{1-4}$ alkyl groups may be either identical or different);
wherein Ar$^1$ and Ar$^2$ are independently a divalent group selected from the group consisting of an aryl group in which some of hydrogen atoms may be substituted with a halogen atom, an alkyl group having 2 to 5 carbon atoms, an alkoxy group having 2 to 4 carbon atoms, an alkenyl group having 3 to 7 carbon atoms, an alkynyl group having 3 to 7 carbon atoms, an aryl group in which some of hydrogen atoms may be substituted with an alkyl group having 1 to 6 carbon atoms, an alkoxy group having 1 to 6 carbon atoms, or a halogen atom, an aryl group in which some of hydrogen atoms are substituted with an aryl group in which some of hydrogen atoms may be substituted with an alkyl group having 1 to 6 carbon atoms, an alkoxy group having 1 to 6 carbon atoms, or a halogen atom, an aryl group in which some of hydrogen atoms are substituted with a heteroaryl group in which some of hydrogen atoms may be substituted with an alkyl group having 1 to 6 carbon atoms, an alkoxy group having 1 to 6 carbon atoms, or a halogen atom, a heteroaryl group in which some of hydrogen atoms may be substituted with an alkyl group having 1 to 6 carbon atoms, an alkoxy group having 1 to 6 carbon atoms, or a halogen atom, a heteroaryl group in which some of hydrogen atoms are substituted with an aryl group in which some of hydrogen atoms may be substituted with an alkyl group having 1 to 6 carbon atoms, an alkoxy group having 1 to 6 carbon atoms, or a halogen atom, an heteroaryl group in which some of hydrogen atoms may be substituted with a heteroaryl group in which some of hydrogen atoms may be substituted with an alkyl group having 1 to 6 carbon atoms, an alkoxy group having 1 to 6 carbon atoms, or a halogen atom, and a heteroaryl group in which some of hydrogen atoms may be substituted with an alkyl group having 1 to 4 carbon atoms, an alkoxy group having 1 to 3 carbon atoms, or a halogen atom; and wherein $Z^1$ and $Z^2$ are independently a group selected from the group consisting of a hydrogen atom, a halogen atom, an alkyl group having 1 to 4 carbon atoms, and an alkoxy group having 1 to 3 carbon atoms, provided that $Z^1$ and $Z^2$ may be bonded to each other to form a single bond or a divalent hydrocarbon group.

3. The method according to 1 or 2 above, wherein the aromatic compound having the amino group is a compound represented by a general formula (21), and the compound produced by the method is a compound represented by a general formula (22),

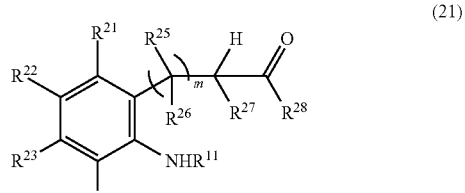

(21)

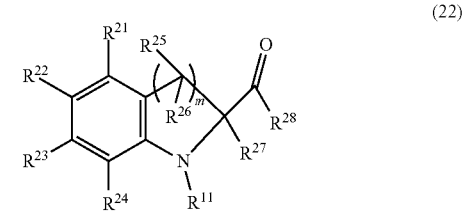

(22)

wherein m is 1 or 2, $R^{11}$ is a hydrogen atom, a tert-butoxycarbonyl group, a benzyloxycarbonyl group, a 2,2,2-trichloroethoxycarbonyl group, or a methanesulfonyl group, $R^{25}$ and $R^{26}$ are independently a hydrogen atom or a linear, branched or cyclic hydrocarbon group having 1 to 20 carbon atoms in which some of hydrogen atoms may be substituted with a halogen atom, $R^{27}$ is a hydrogen atom or a linear, branched or cyclic hydrocarbon group having 1 to 20 carbon atoms in which some of hydrogen atoms may be substituted with a halogen atom, $R^{28}$ is a heteroaryl group having 3 to 20 carbon atoms, a derivative group thereof, or a linear, branched or cyclic hydrocarbon group having 1 to 20 carbon atoms in which some of hydrogen atoms may be substituted with a halogen atom, and $R^{21}$, $R^{22}$, $R^{23}$ and $R^{24}$ are independently a hydrogen atom, a halogen atom, an alkoxy group having 1 to 10 carbon atoms, or a linear, branched or cyclic hydrocarbon group having 1 to 20 carbon atoms in which some of hydrogen atoms may be substituted with a halogen atom, provided that one, two or all of the combinations of $R^{21}$ and $R^{22}$, $R^{22}$ and $R^{23}$, and $R^{23}$ and $R^{24}$ may be bonded to each other to form a divalent organic group.

4. The method according to 1 or 2 above, wherein the aromatic compound having the carboxyl group is a compound represented by a general formula (41) or (42), and the compound produced by the method is a compound represented by a general formula (43) or (44),

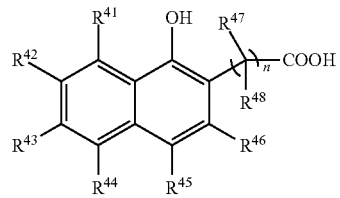

(41)

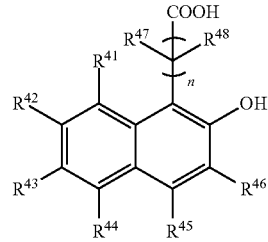

(42)

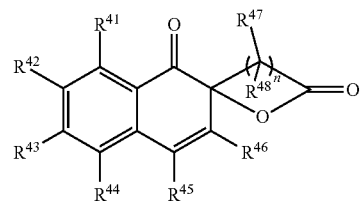

(43)

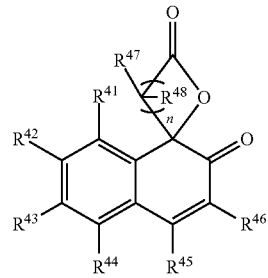

(44)

wherein n is 2 or 3, $R^{47}$ and $R^{48}$ are independently a hydrogen atom or a linear, branched or cyclic hydrocarbon group having 1 to 20 carbon atoms in which some of hydrogen atoms may be substituted with a halogen atom, and $R^{41}$, $R^{42}$, $R^{43}$, $R^{44}$, $R^{45}$ and $R^{46}$ are independently a hydrogen atom, a halogen atom, an alkoxy group having 1 to 10 carbon atoms, or a linear, branched or cyclic hydrocarbon group having 1 to 20 carbon atoms in which some of hydrogen atoms may be substituted with a halogen atom, provided that one, two, three, four or all of the combinations of $R^{41}$ and $R^{42}$, $R^{42}$ and $R^{43}$, $R^{43}$ and $R^{44}$, $R^{44}$ and $R^{45}$, and $R^{45}$ and $R^{46}$ may be bonded to each other to form a divalent organic group.

Advantageous Effects of the Invention

The present invention thus makes it possible to efficiently produce a compound (e.g., 2-acylindoline or spirolactone) having a ring structure that includes the desired atom.

In the case of utilizing the compound represented by the general formula (2) as the quaternary ammonium salt, an optically active compound can be produced with high enantioselectivity.

In the case of utilizing the amino group-containing aromatic compound represented by the general formula (21) as the substrate, the compound represented by the general formula (22) can be efficiently produced. A compound having a 5-membered ring structure that includes the nitrogen atom included in —NHR$^{11}$ is obtained when m in the general formula (21) is 1, and a compound having a 6-membered ring structure that includes the nitrogen atom included in —NHR$^{11}$ is obtained when m in the general formula (21) is 2.

In the case of utilizing the carboxyl group-containing aromatic compound represented by the general formula (41) or (42) as the substrate, the compound represented by the general formula (43) or (44) can be efficiently produced. A compound having a 5-membered ring structure that includes one oxygen atom among the oxygen atoms included in the carboxyl group is obtained when n in the general formula (41) or (42) is 2, and a compound having a 6-membered ring structure that includes one oxygen atom among the oxygen atoms included in the carboxyl group is obtained when n in the general formula (41) or (42) is 3.

DESCRIPTION OF EMBODIMENTS

The present invention is a method in which a substrate is reacted in a system that is supplied with a quaternary ammonium salt represented by the above-mentioned general formula (1) and an oxidizing agent to produce a compound having a ring structure, the substrate is an aromatic compound in which an amino group represented by —NHR$^{11}$ (wherein R$^{11}$ is a hydrogen atom, a tert-butoxycarbonyl group, a benzyloxycarbonyl group, a 2,2,2-trichloroethoxycarbonyl group, or a methanesulfonyl group) and —R$^{13}$—CHR$^{15}$—C(O)—R$^{17}$ (wherein R$^{13}$ is a divalent hydrocarbon group in which some of hydrogen atoms may be substituted with a substituent, R$^{15}$ is a hydrogen atom or a linear, branched or cyclic hydrocarbon group having 1 to 20 carbon atoms in which some of hydrogen atoms may be substituted with a halogen atom, and R$^{17}$ is a heteroaryl group having 3 to 20 carbon atoms, a derivative group thereof, or a linear, branched or cyclic hydrocarbon group having 1 to 20 carbon atoms in which some of hydrogen atoms may be substituted with a halogen atom) are respectively bonded to two adjacent carbon atoms that form a benzene ring (hereinafter referred to as "amino group-containing aromatic compound"), or an aromatic compound in which a hydroxyl group and a carboxyl group are respectively bonded to carbon atoms that form a naphthalene ring and are situated at position 1 or 2, the carboxyl group is bonded via a chain hydrocarbon group in which some of hydrogen atoms may be substituted with a halogen atom (hereinafter referred to as "carboxyl group-containing aromatic compound"), the ring structure including a nitrogen atom derived from the amino group or an oxygen atom derived from the carboxyl group.

First, the quaternary ammonium salt represented by the general formula (1) and the oxidizing agent are described.

R$^1$, R$^2$, R$^3$ and R$^4$ in the general formula (1) that represents the quaternary ammonium salt are independently a hydrocarbon group or a heteroatom-containing hydrocarbon group (e.g., heteroalkyl group or heteroaryl group) having 1 to 30 (preferably 2 to 8) carbon atoms in which some of hydrogen atoms may be substituted with a halogen atom. When at least one of R$^1$, R$^2$, R$^3$ and R$^4$ is a group in which some of hydrogen atoms are substituted with a halogen atom, the halogen atom may be a fluorine atom, a chlorine atom, or the like.

In the general formula (1), all of R$^1$, R$^2$, R$^3$ and R$^4$ may be an identical group, or three of R$^1$, R$^2$, R$^3$ and R$^4$ may be an identical group, or two of R$^1$, R$^2$, R$^3$ and R$^4$ and the remainder of R$^1$, R$^2$, R$^3$ and R$^4$ may respectively be an identical group, or two of R$^1$, R$^2$, R$^3$ and R$^4$ may be an identical group, and the remainder of R$^1$, R$^2$, R$^3$ and R$^4$ may be different groups, or all of R$^1$, R$^2$, R$^3$ and R$^4$ may be different groups.

A compound having a ring structure that includes a nitrogen atom or an oxygen atom can be produced from the substrate in high yield by utilizing the quaternary ammonium salt represented by the general formula (1) wherein R$^1$, R$^2$, R$^3$ and R$^4$ are a hydrocarbon group (unsubstituted hydrocarbon group (e.g., alkyl group, aralkyl group, or aryl group)) having 1 to 30 carbon atoms.

R$^1$ and R$^2$ in the general formula (1) may be bonded to each other to form a divalent organic group (herein after referred to as "organic group (G1)") that is bonded to the nitrogen atom, and R$^3$ and R$^4$ in the general formula (1) may be bonded to each other to form a divalent organic group (herein after referred to as "organic group (G2)") that is bonded to the nitrogen atom. The organic groups (G1) and (G2) may be either identical or different.

Examples of the organic groups (G1) and (G2) include —(CH$_2$)$_y$— (wherein y is an integer from 2 to 8), groups represented by the following formulae, and the like.

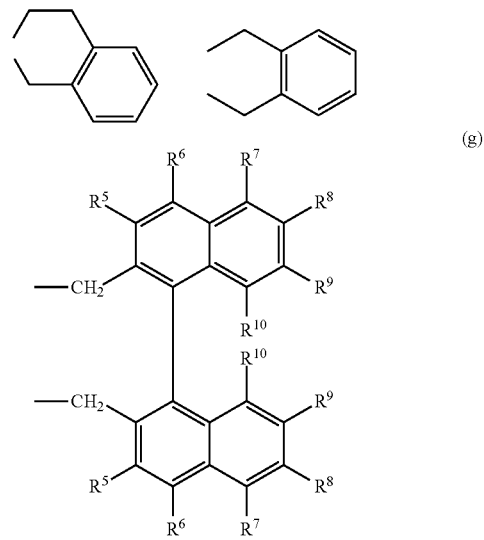

(g)

(In the formula, R$^5$, R$^6$, R$^7$, R$^8$, R$^9$ and R$^{10}$ are independently a group selected from the group consisting of a hydrogen atom, a linear, branched or cyclic alkyl group having 1 to 6 carbon atoms in which some of hydrogen atoms may be substituted with a halogen atom, a linear, branched or cyclic alkenyl group having 2 to 6 carbon atoms in which some of hydrogen atoms may be substituted with a halogen atom, a linear, branched or cyclic alkynyl group having 2 to 6 carbon atoms in which some of hydrogen atoms may be substituted with a halogen atom, an aralkyl group in which some of hydrogen atoms may be substituted with an alkyl group having 1 to 4 carbon atoms in which some of hydrogen atoms may be substituted with a halogen atom, an alkoxy group having 1 to 3 carbon atoms in which some of hydrogen atoms may be substituted with a halogen atom, or a halogen atom, a heteroaralkyl group in which some of hydrogen atoms may be substituted with an alkyl group having 1 to 4 carbon atoms in which some of hydrogen atoms may be substituted with a halogen atom, an alkoxy group having 1 to 3 carbon atoms in which some of hydrogen atoms may be substituted with a halogen atom, or a halogen atom, an aryl group in which some of hydrogen atoms may be substituted with an alkyl group having 1 to 4 carbon atoms in which some of hydrogen atoms may be substituted with a halogen atom, an alkoxy group having 1 to 3 carbon atoms in which some of hydrogen atoms may be substituted with a halogen atom, or a halogen atom, an aryl group in which some of hydrogen atoms are substituted with an aryl group that may be substituted with an alkyl group having 1 to 4 carbon atoms in which some of hydrogen atoms may be substituted with a halogen atom, a heteroaryl group in which some of hydrogen atoms may be substituted with an alkyl group having 1 to 4 carbon atoms in which some of hydrogen atoms may be substituted with a halogen atom, an alkoxy group having 1 to 3 carbon atoms in which some of hydrogen atoms may be substituted with a halogen atom, or a halogen atom, a ($C_{1-3}$ alkoxy)carbonyl group, an N—($C_{1-4}$ alkyl)carbonyl group, a carbamoyl group, an N—($C_{1-4}$ alkyl)carbamoyl group, and an N,N-di($C_{1-4}$ alkyl)carbamoyl group (wherein the $C_{1-4}$ alkyl groups may be either identical or different.)

The linear, branched, or cyclic alkyl group having 1 to 6 carbon atoms represented by $R^5$, $R^6$, $R^7$, $R^8$, $R^9$ and $R^{10}$ refers to a linear, branched, or cyclic alkyl group having an arbitrary number of carbon atoms within the range of 1 to 6. Example thereof includes a methyl group, an ethyl group, an n-propyl group, an isopropyl group, a cyclopropyl group, an n-butyl group, a sec-butyl group, a tert-butyl group, a cyclobutyl group, a pentyl group, a cyclopentyl group, a hexyl group, a cyclohexyl group, and the like.

The linear, branched, or cyclic alkenyl group having 2 to 6 carbon atoms represented by $R^5$, $R^6$, $R^7$, $R^8$, $R^9$ and $R^{10}$ refers to a linear, branched, or cyclic alkenyl group having an arbitrary number of carbon atoms within the range of 2 to 6. Example thereof includes an ethenyl group, a propenyl group, an isopropenyl group, a butenyl group, a 1-methyl-1-propenyl group, a 1-methyl-2-propenyl group, a 2-methyl-1-propenyl group, a 2-methyl-2-propenyl group, a cyclobutenyl group, a pentenyl group, a cyclopentenyl group, a hexenyl group, a cyclohexenyl group, and the like.

The linear, branched, or cyclic alkynyl group having 2 to 6 carbon atoms represented by $R^5$, $R^6$, $R^7$, $R^8$, $R^9$ and $R^{10}$ refers to a linear, branched, or cyclic alkynyl group having an arbitrary number of carbon atoms within the range of 2 to 6. Example thereof includes an ethynyl group, a propynyl group, a cyclopropylethynyl group, a butynyl group, a 1-methyl-2-propynyl group, a pentynyl group, a cyclobutylethynyl group, a hexynyl group, and the like.

Examples of the aralkyl group include a benzyl group, a phenethyl group, a naphthylmethyl group, and the like.

Examples of the heteroaralkyl group include a pyridylmethyl group, an indolylmethyl group, a furylmethyl group, a thienylmethyl group, a pyrrolylmethyl group, and the like.

Examples of the aryl group include a phenyl group, a naphthyl group, and the like.

Examples of the aryl group which is substituted with an aryl group that may be substituted with an alkyl group having 1 to 4 carbon atoms in which some of hydrogen atoms may be substituted with a halogen atom, include a 3,5-diphenylphenyl group, a 3,5-di(3,5-di-tert-butylphenyl)phenyl group, 3,5-bis(3,5-bis(trifluoromethyl)phenyl)phenyl group, and the like.

Examples of the heteroaryl group include a pyridyl group, a pyrrolyl group, an imidazolyl group, a furyl group, an indolyl group, a thienyl group, an oxazolyl group, a thiazolyl group, a tetrazolyl group, and the like.

Examples of the halogen atom that may substitute some of hydrogen atoms in the hydrocarbon group, the heteroatom-containing group, and the like represented by $R^5$, $R^6$, $R^7$, $R^8$, $R^9$ and $R^{10}$ include a fluorine atom, a chlorine atom, and the like.

$R^5$, $R^6$, $R^7$, $R^8$, $R^9$ and $R^{10}$ in the general formula (g) may respectively be either identical or different.

When the quaternary ammonium salt represented by the general formula (1) has the organic groups (G1) and (G2), it is preferably an N-spiro quaternary ammonium salt represented by the following general formula (2). When the N-spiro quaternary ammonium salt is used, the N-spiro quaternary ammonium salt also serves as a phase transfer catalyst when producing a compound having a ring structure that includes a nitrogen atom or an oxygen atom from the substrate, so that high enantioselectivity can be achieved.

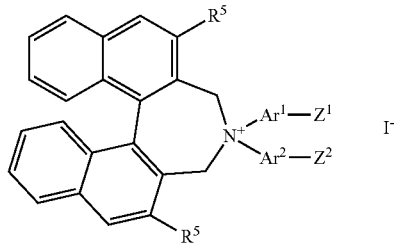

(2)

(In the formula, $R^5$ is the same as defined above, $Ar^1$ and $Ar^2$ are independently a divalent group selected from the group consisting of an aryl group in which some of hydrogen atoms may be substituted with a halogen atom, an alkyl group having 2 to 5 carbon atoms, an alkoxy group having 2 to 4 carbon atoms, an alkenyl group having 3 to 7 carbon atoms, an alkynyl group having 3 to 7 carbon atoms, an aryl group in which some of hydrogen atoms may be substituted with an alkyl group having 1 to 6 carbon atoms, an alkoxy group having 1 to 6 carbon atoms, or a halogen atom, an aryl group in which some of hydrogen atoms are substituted with an aryl group in which some of hydrogen atoms may be substituted with an alkyl group having 1 to 6 carbon atoms, an alkoxy group having 1 to 6 carbon atoms, or a halogen atom, an aryl group in which some of hydrogen atoms are substituted with a heteroaryl group in which some of hydrogen atoms may be substituted with an alkyl group having 1 to 6 carbon atoms, an alkoxy group having 1 to 6 carbon atoms, or a halogen atom, a heteroaryl group in which some of hydrogen atoms may be substituted with an alkyl group having 1 to 6 carbon atoms, an alkoxy group having 1 to 6 carbon atoms, or a halogen atom, a heteroaryl group in which some of hydrogen atoms are substituted with an aryl group in which some of hydrogen atoms may be substituted with an alkyl group having 1 to 6 carbon atoms, an alkoxy group having 1 to 6 carbon atoms, or a halogen atom, an heteroaryl group in which some of hydrogen atoms may be substituted with a heteroaryl group in which some of hydrogen atoms may be substituted with an alkyl group having 1 to 6 carbon atoms, an alkoxy group having 1 to 6 carbon atoms, or a halogen atom, and a heteroaryl group in which some of hydrogen atoms may be substituted with an alkyl group having 1 to 4 carbon atoms, an alkoxy group having 1 to 3 carbon atoms, or a halogen atom, and $Z^1$ and $Z^2$ are independently a group selected from the group consisting of a hydrogen atom, a halogen atom, an alkyl group having 1 to 4 carbon atoms, and an alkoxy group having 1 to 3 carbon atoms, provided that $Z^1$ and $Z^2$ may be bonded to each other to form a single bond or a divalent hydrocarbon group.)

It is preferable that —$Ar^1$—$Z^1$ and —$Ar^2$—$Z^2$ which are bonded to the nitrogen atom in the general formula (2) form the divalent group represented by the general formula (g) in which $Z^1$ and $Z^2$ are bonded to each other.

A compound represented by the following general formula (2a) and a compound represented by the following general formula (2b) are preferable as the N-spiro quaternary ammonium salt.

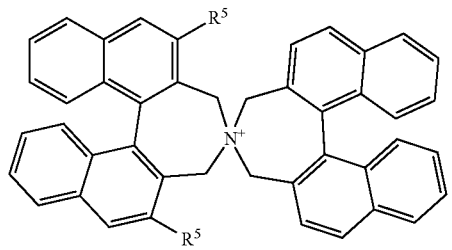

(2a)

(In the formula, $R^5$ is the same as defined above.)

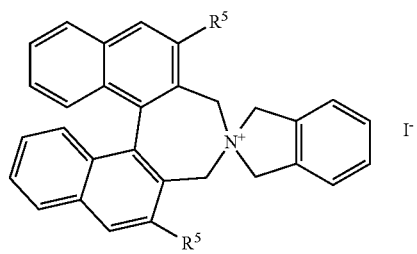

(2b)

(In the formula, $R^5$ is the same as defined above.)

$R^5$ in the general formulae (2a) and (2b) is preferably a hydrogen atom, a phenyl group, a 4-methoxyphenyl group (4-MeOC$_6$H$_5$), a 4-trifluoromethylphenyl group (4-(CF$_3$)C$_6$H$_5$), a 3,4,5-trifluorophenyl group, a 3,4,5-trichlorophenyl group, a 3,4-difluorophenyl group, a 3-nitrophenyl group, a 3-cyanophenyl group, a benzothiophenyl-2-yl group, a 3,5-difluorophenyl group, a 3-trifluoromethylphenyl group, a 2,4-difluorophenyl group, a 3-methylsulfonylphenyl group, a 2,3-bis(trifluoromethyl)phenyl group, a 3,5-bistrifluoromethylphenyl group (3,5-(CF$_3$)$_2$C$_6$H$_3$), a 3,5-bis(3,5-bistrifluoromethylphenyl)phenyl group (3,5-[3,5-(CF$_3$)$_2$ C$_6$H$_3$]$_2$C$_6$H$_3$), a 3,4,5-trifluorophenyl group (3,4,5-F$_3$C$_3$H$_3$), a 4-(3,5-bistrifluoromethylphenyl)phenyl group (4-[3,5-(CF$_3$)$_2$C$_6$H$_3$]C$_6$H$_4$), a 4-(4-trifluoromethylphenyl)phenyl group (4-(4-CF$_3$C$_6$H$_4$)C$_6$H$_4$), or the like.

The amount of the quaternary ammonium salt used in the present invention is appropriately selected depending on the type of the substrate, but is normally in the range from 0.01 to 0.5 equivalent based on the substrate.

Examples of the oxidizing agent used in combination with the quaternary ammonium salt include hydrogen peroxide, a urea-hydrogen peroxide adduct (UHP), tert-butyl hydroperoxide, di-tert-butyl peroxide, tert-amyl hydroperoxide, di-tert-amyl peroxide, cumene hydroperoxide, dicumyl peroxide, tert-butylcumyl peroxide, tert-butyl peroxypivalate, benzoyl peroxide, lauroyl peroxide, ethylbenzene hydroperoxide, peracetic acid, perbenzoic acid, and the like. These compounds may be used singly or in combination of two or more types thereof.

The amount of the oxidizing agent used in the present invention is appropriately selected depending on the type of the substrate, but is normally in the range from 100 to 400 equivalents based on the substrate.

Next, a method for producing a 2-acylindoline using an amino group-containing aromatic compound as the substrate, and a method for producing a spirolactone using a carboxyl group-containing aromatic compound as the substrate are described.

The amino group-containing aromatic compound is a compound in which an amino group represented by —NHR$^{11}$ (wherein R$^{11}$ is a hydrogen atom, a tert-butoxycarbonyl group, a benzyloxycarbonyl group, a 2,2,2-trichloroethoxycarbonyl group, or a methanesulfonyl group) and —R$^{13}$—CHR$^{15}$—C(O)—R$^{15}$—C(O)—R$^{17}$ (wherein R$^{13}$ is a divalent hydrocarbon group in which some of hydrogen atoms may be substituted with a substituent, R$^{15}$ is a hydrogen atom or a linear, branched or cyclic hydrocarbon group having 1 to 20 carbon atoms in which some of hydrogen atoms may be substituted with a halogen atom, and R$^{17}$ is a heteroaryl group having 3 to 20 carbon atoms, a derivative group thereof, or a linear, branched or cyclic hydrocarbon group having 1 to 20 carbon atoms in which some of hydrogen atoms may be substituted with a halogen atom) are respectively bonded to two adjacent carbon atoms that form a benzene ring. The amino group-containing aromatic compound is preferably a compound represented by the following general formula (21) (hereinafter referred also to as "aniline derivative").

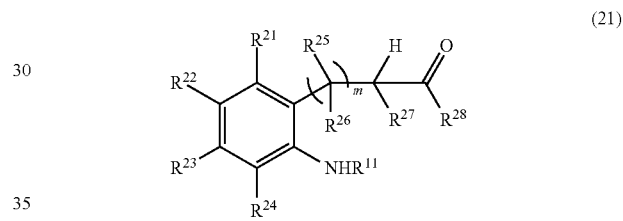

(21)

(In the formula, m is 1 or 2, R$^{11}$ is a hydrogen atom, a tert-butoxycarbonyl group, a benzyloxycarbonyl group, a 2,2,2-trichloroethoxycarbonyl group, or a methanesulfonyl group, R$^{25}$ and R$^{26}$ are independently a hydrogen atom or a linear, branched or cyclic hydrocarbon group having 1 to 20 carbon atoms in which some of hydrogen atoms may be substituted with a halogen atom, R$^{27}$ is a hydrogen atom or a linear, branched or cyclic hydrocarbon group having 1 to 20 carbon atoms in which some of hydrogen atoms may be substituted with a halogen atom, R$^{28}$ is a heteroaryl group having 3 to 20 carbon atoms, a derivative group thereof, or a linear, branched or cyclic hydrocarbon group having 1 to 20 carbon atoms in which some of hydrogen atoms may be substituted with a halogen atom, and R$^{21}$, R$^{22}$, R$^{23}$ and R$^{24}$ are independently a hydrogen atom, a halogen atom, an alkoxy group having 1 to 10 carbon atoms, or a linear, branched or cyclic hydrocarbon group having 1 to 20 carbon atoms in which some of hydrogen atoms may be substituted with a halogen atom, provided that one, two or all of the combinations of R$^{21}$ and R$^{22}$, R$^{22}$ and R$^{23}$, and R$^{23}$ and R$^{24}$ may be bonded to each other to form a divalent organic group.)

In the general formula (21), —(C(R$^{25}$)(R$^{26}$))$_m$— in the general formula (21) corresponds to R$^{13}$, and R$^{27}$ and R$^{28}$ respectively correspond to R$^{15}$ and R$^{17}$.

When at least one of R$^{21}$, R$^{22}$, R$^{23}$, R$^{24}$, R$^{25}$, R$^{26}$, R$^{27}$ and R$^{28}$ in the general formula (21) includes a hydrocarbon group having 1 to 20 carbon atoms, the hydrocarbon group may be an aliphatic hydrocarbon group, an alicyclic hydrocarbon group, or an aromatic hydrocarbon group.

When at least one of $R^{21}$, $R^{22}$, $R^{23}$ and $R^{24}$ in the general formula (21) is a halogen atom, the halogen atom may be a fluorine atom, a chlorine atom, a bromine atom, or an iodine atom.

When at least one of $R^{21}$, $R^{22}$, $R^{23}$ and $R^{24}$ in the general formula (21) is a group in which some of hydrogen atoms are substituted with a halogen atom, the halogen atom may be a fluorine atom, a chlorine atom, a bromine atom, or an iodine atom.

When at least one of $R^{21}$, $R^{22}$, $R^{23}$ and $R^{24}$ in the general formula (21) includes an alkoxy group having 1 to 10 carbon atoms, R (hydrocarbon group) in —OR may be an aliphatic hydrocarbon group, an alicyclic hydrocarbon group, or an aromatic hydrocarbon group. Examples of the alkoxy group include a methoxy group, an ethoxy group, a propoxy group, a butoxy group, and the like.

In the general formula (21), all of $R^{21}$, $R^{22}$, $R^{23}$ and $R^{24}$ may be an identical group, or three of $R^{21}$, $R^{22}$, $R^{23}$ and $R^{24}$ may be an identical group, or two of $R^{21}$, $R^{22}$, $R^{23}$ and $R^{24}$ and the remainder of $R^{21}$, $R^{22}$, $R^{23}$ and $R^{24}$ may respectively be an identical group, or two of $R^{21}$, $R^{22}$, $R^{23}$ and $R^{24}$ may be an identical group, and the remainder of $R^{21}$, $R^{22}$, $R^{23}$ and $R^{24}$ may be different groups, or all of $R^{21}$, $R^{22}$, $R^{23}$ and $R^{24}$ may be different groups.

$R^{25}$ and $R^{26}$ in the general formula (21) may be either identical or different.

When m in the general formula (21) is 2, $R^{25}$ and $R^{26}$ may respectively be either identical or different.

Examples of the heteroaryl group having 3 to 20 carbon atoms represented by $R^{28}$ in the general formula (21) include a pyridyl group, a pyrrolyl group, an imidazolyl group, a quinolyl group, a triazolyl group, a pyrazolyl group, and the like.

The derivative group of the heteroaryl group may be a group (e.g., N-phenylimidazolyl group or N-methylimidazolyl group) in which an alkyl group having 1 to 10 carbon atoms, or an aryl group in which some of hydrogen atoms are substituted with an alkyl group having 1 to 6 carbon atoms, an alkoxy group having 1 to 6 carbon atoms, or a halogen atom is bonded to the carbon atom or the nitrogen atom that forms the ring structure of the heteroaryl group.

A compound represented by the following general formula (22) (i.e., 2-acylindoline) can be produced by reacting the compound (aniline derivative) represented by the general formula (21) as the amino group-containing aromatic compound (substrate) in a system that is supplied with the quaternary ammonium salt represented by the general formula (1) and the oxidizing agent via an intramolecular oxidative cyclization reaction.

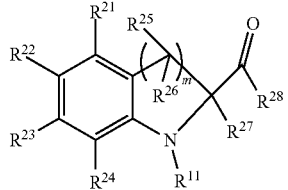

(22)

(In the formula, m, $R^{11}$, $R^{21}$, $R^{22}$, $R^{23}$, $R^{24}$, $R^{25}$, $R^{26}$, $R^{27}$ and $R^{28}$ are the same as defined above.)

In the following, the 2-acylindoline production conditions and the like are described.

The aniline derivative (substrate) is reacted in the system that is supplied with the quaternary ammonium salt and the oxidizing agent. The substrate may be supplied to a reactor that is charged with the quaternary ammonium salt and the oxidizing agent in advance, and reacted at a given temperature, or all of the components may be supplied to a reactor together to effect a reaction.

It is conjectured that the reaction mechanism of the substrate includes (i) a reaction in which the quaternary ammonium salt is oxidized by the oxidizing agent in the reaction system that is supplied with the quaternary ammonium salt and the oxidizing agent to form a "quaternary ammonium salt containing catalyst" (the structure of the catalyst is unknown, but is considered to be $R_4N^{+}.^{-}OI$ or $R_4N^{+}.^{-}OIO$) (hereinafter referred also to as "catalyst"), and the substrate is subjected to oxidization and an intramolecular oxidative cyclization reaction in the presence of the catalyst to form the compound represented by the general formula (22), and (ii) a reaction in which the catalyst is decomposed (reduced), and the quaternary ammonium salt is regenerated due to dehydration during the intramolecular oxidative cyclization reaction. Therefore, it is conjectured that the quaternary ammonium salt supplied to the reaction system serves as a "catalyst precursor". The amount of the quaternary ammonium salt supplied to the reaction system is determined as described above by applying the amount of a catalyst used for a normal organic synthesis reaction to the amount of the catalyst precursor. Since the oxidizing agent supplied to the reaction system is in excess and is not consumed only by oxidation of the quaternary ammonium salt, it is conjectured that the oxidizing agent acts on the substrate as a "co-oxidizing agent" together with the above quaternary ammonium salt containing catalyst.

The reaction for producing the 2-acylindoline is normally effected in a solvent such as an aliphatic hydrocarbon-based ester, an ether, an aliphatic hydrocarbon-based nitrile, a nitroalkane, and an aromatic hydrocarbon. These compounds may be used singly or in combination of two or more types thereof.

Examples of the aliphatic hydrocarbon-based ester include methyl acetate, ethyl acetate, n-propyl acetate, isopropyl acetate, n-butyl acetate, isobutyl acetate, tert-butyl acetate, and the like.

Examples of the ether include diethyl ether, diisopropyl ether, methyl tert-butyl ether, tetrahydrofuran, 1,2-dimethoxyethane, 1,2-diethoxyethane, dioxane, cyclopentyl methyl ether, and the like.

Examples of the aliphatic hydrocarbon-based nitrile include acetonitrile, propionitrile, butyronitrile, and the like.

Examples of the nitroalkane include nitromethane, nitroethane, and the like.

Examples of the aromatic hydrocarbon include toluene, benzene, mesitylene, and the like.

The solvent is used in such an amount that the concentration of the substrate is preferably in the range from 0.001 to 0.5 mol/L, and more preferably from 0.05 to 0.2 mol/L.

The reaction temperature is appropriately selected depending on the type of the solvent and the like, but is preferably in the range from −10° C. to 100° C., and more preferably from 0° C. to 50° C., from the viewpoint of the reaction efficiency.

The atmosphere inside the reaction system may be air, inert gas, or the like.

After completion of the reaction, the product may optionally be subjected to a normal post-treatment (e.g., removal of the solvent, washing of the product, and chromatographic separation).

The embodiments of the present invention can improve the yield of the 2-acylindoline calculated based on the molar quantity of the aniline derivative (substrate) to 15% or higher.

The yield can preferably be improved to 50% or higher (particularly preferably 70% or higher).

It is possible to achieve excellent enantioselectivity by utilizing the N-spiro quaternary ammonium salt represented by the general formula (2) as the quaternary ammonium salt, so that the enantioselectivity can preferably be improved to 40% or higher (more preferably 60% or higher, and particularly preferably 70% or higher).

On the other hand, the carboxyl group-containing aromatic compound is a compound in which a hydroxyl group and a carboxyl group are respectively bonded to carbon atoms that form a naphthalene ring and are situated at position 1 or 2, the carboxyl group is bonded via a chain hydrocarbon group in which some of hydrogen atoms may be substituted with a halogen atom. The carboxyl group-containing aromatic compound is preferably a compound represented by the following general formula (41) or (42) (hereinafter referred also to as "naphthol derivative").

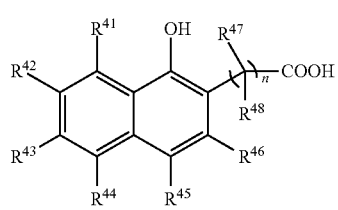

(41)

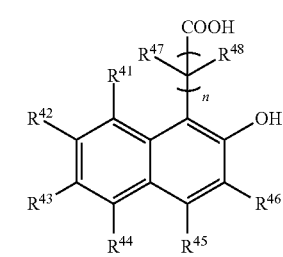

(42)

(In the formulae, n is 2 or 3, $R^{47}$ and $R^{48}$ are independently a hydrogen atom or a linear, branched or cyclic hydrocarbon group having 1 to 20 carbon atoms in which some of hydrogen atoms may be substituted with a halogen atom, and $R^{41}$, $R^{42}$, $R^{43}$, $R^{44}$, $R^{45}$ and $R^{46}$ are independently a hydrogen atom, a halogen atom, an alkoxy group having 1 to 10 carbon atoms, or a linear, branched or cyclic hydrocarbon group having 1 to 20 carbon atoms in which some of hydrogen atoms may be substituted with a halogen atom, provided that one, two, three, four or all of the combinations of $R^{41}$ and $R^{42}$, $R^{42}$ and $R^{43}$, $R^{43}$ and $R^{44}$, $R^{44}$ and $R^{45}$, and $R^{45}$ and $R^{46}$ may be bonded to each other to form a divalent organic group.)

When at least one of $R^{41}$, $R^{42}$, $R^{43}$, $R^{44}$, $R^{45}$ and $R^{46}$ in the general formulae (41) and (42) includes a hydrocarbon group having 1 to 20 carbon atoms, the hydrocarbon group may be an aliphatic hydrocarbon group, an alicyclic hydrocarbon group, or an aromatic hydrocarbon group.

When at least one of $R^{41}$, $R^{42}$, $R^{43}$, $R^{44}$, $R^{45}$ and $R^{46}$ in the general formulae (41) and (42) is a halogen atom, the halogen atom may be a fluorine atom, a chlorine atom, a bromine atom, or an iodine atom.

When at least one of $R^{41}$, $R^{42}$, $R^{43}$, $R^{44}$, $R^{45}$ and $R^{46}$ in the general formulae (41) and (42) is a group in which some of hydrogen atoms are substituted with a halogen atom, the halogen atom may be a fluorine atom, a chlorine atom, or the like.

When at least one of $R^{41}$, $R^{42}$, $R^{43}$, $R^{44}$, $R^{45}$ and $R^{46}$ in the general formulae (41) and (42) is an alkoxy group having 1 to 10 carbon atoms, R (hydrocarbon group) in —OR may be an aliphatic hydrocarbon group, an alicyclic hydrocarbon group, or an aromatic hydrocarbon group. Examples of the alkoxy group include a methoxy group, an ethoxy group, a propoxy group, a butoxy group, and the like.

In the general formulae (41) and (42), all of $R^{41}$, $R^{42}$, $R^{43}$, $R^{44}$, $R^{45}$ and $R^{46}$ may be an identical group, or five of $R^{41}$, $R^{42}$, $R^{43}$, $R^{44}$, $R^{45}$ and $R^{46}$ may be an identical group, four of $R^{41}$, $R^{42}$, $R^{43}$, $R^{44}$, $R^{45}$ and $R^{46}$ may be an identical group, three of $R^{41}$, $R^{42}$, $R^{43}$, $R^{44}$, $R^{45}$ and $R^{46}$ may be an identical group (and the remainder of $R^{41}$, $R^{42}$, $R^{43}$, $R^{44}$, $R^{45}$ and $R^{46}$ may be an identical group), or two of $R^{41}$, $R^{42}$, $R^{43}$, $R^{44}$, $R^{45}$ and $R^{46}$ may be an identical group (and the remainder of $R^{41}$, $R^{42}$, $R^{43}$, $R^{44}$, $R^{45}$ and $R^{46}$ may be an identical group), or all of $R^{41}$, $R^{42}$, $R^{43}$, $R^{44}$, $R^{45}$ and $R^{46}$ may be different groups.

$R^{47}$ and $R^{48}$ in the general formulae (41) and (42) may be either identical or different.

When n in the general formulae (41) and (42) is 2, $R^{47}$ and $R^{48}$ may respectively be either identical or different.

When n in the general formulae (41) and (42) is 3, $R^{47}$ and $R^{48}$ may respectively be either identical or different.

A compound represented by the following general formula (43) or (44) (i.e., spirolactone) can be produced by reacting the compound (naphthol derivative) represented by the general formula (41) or (42) as the carboxyl group-containing aromatic compound (substrate) in a system that is supplied with the quaternary ammonium salt represented by the general formula (1) and the oxidizing agent via an intramolecular oxidative cyclization reaction.

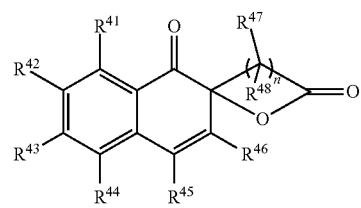

(43)

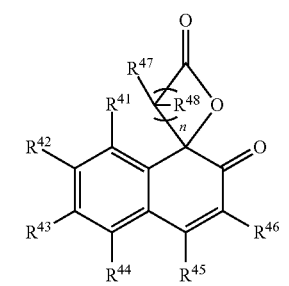

(44)

(In the formulae, n, $R^{41}$, $R^{42}$, $R^{43}$, $R^{44}$, $R^{45}$, $R^{46}$, $R^{47}$ and $R^{48}$ are the same as defined above.)

The spirolactone production conditions and the like are described below.

The carboxyl group-containing aromatic compound (substrate) is reacted in the system that is supplied with the quaternary ammonium salt and the oxidizing agent. The substrate may be supplied to a reactor that is charged with the quaternary ammonium salt and the oxidizing agent in advance, and reacted at a given temperature, or all of the components may be supplied to a reactor together to effect a reaction.

It is conjectured that the reaction mechanism of the substrate includes (i) a reaction in which the quaternary ammonium salt is oxidized by the oxidizing agent in the reaction system that is supplied with the quaternary ammonium salt and the oxidizing agent to form a "quaternary ammonium salt containing catalyst" (the structure of the catalyst is unknown, but is considered to be $R_4N^+ \cdot OI$ or $R_4N^+ \cdot {}^-OIO$) (hereinafter referred also to as "catalyst"), and the substrate is subjected to oxidization and an intramolecular oxidative cyclization reaction in the presence of the catalyst to form the compound represented by the general formula (43) or (44), and (ii) a reaction in which the catalyst is decomposed (reduced), and the quaternary ammonium salt is regenerated due to dehydration during the intramolecular oxidative cyclization reaction. Therefore, it is conjectured that the quaternary ammonium salt supplied to the reaction system serves as a "catalyst precursor". The amount of the quaternary ammonium salt supplied to the reaction system is determined as described above by applying the amount of a catalyst used for a normal organic synthesis reaction to the amount of the catalyst precursor. Since the oxidizing agent supplied to the reaction system is in excess and is not consumed only by oxidation of the quaternary ammonium salt, it is conjectured that the oxidizing agent acts on the substrate as a "co-oxidizing agent" together with the above quaternary ammonium salt containing catalyst.

The reaction for producing the spirolactone is normally effected in a solvent that mainly includes a hydrocarbon, an aliphatic hydrocarbon-based ester, an aliphatic hydrocarbon-based nitrile, or the like. These compounds may be used singly or in combination of two or more types thereof. It is preferable to use a hydrocarbon as the solvent.

Examples of the hydrocarbon include an aliphatic hydrocarbon having 5 or more carbon atoms, an alicyclic hydrocarbon having a ring that includes 5 or more carbon atoms, an aromatic hydrocarbon having 6 or more carbon atoms, and the like.

Examples of the aliphatic hydrocarbon-based ester include methyl acetate, ethyl acetate, n-propyl acetate, isopropyl acetate, n-butyl acetate, isobutyl acetate, tert-butyl acetate, and the like.

Examples of the aliphatic hydrocarbon-based nitrile include acetonitrile, propionitrile, butyronitrile, and the like.

When the solvent includes a hydrocarbon, it is preferable to use a hydrocarbon that is immiscible with water and water or an inorganic salt aqueous solution in combination. In this case, the quaternary ammonium salt serves as a phase transfer catalyst.

Examples of the inorganic salt used to prepare the inorganic salt aqueous solution include sodium chloride, lithium chloride, potassium chloride, calcium chloride, sodium bromide, lithium bromide, potassium bromide, calcium bromide, and the like. The concentration of the inorganic salt is preferably in the range from 0.1 to 2.0 mol/L, and more preferably from 0.5 to 1.0 mol/L.

The hydrocarbon and water or the inorganic salt aqueous solution are preferably used in an amount of 10 to 90 vol % and 10 to 90 vol % (more preferably 40 to 80 vol % and 20 to 60 vol %), respectively, based on the total amount (=100 vol %) of the hydrocarbon and water or the inorganic salt aqueous solution, from the viewpoint of the reaction efficiency.

When the solvent includes a hydrocarbon that is immiscible with water and water or an inorganic salt aqueous solution, it is possible to obtain a spirolactone with excellent enantioselectivity.

The solvent is used in such an amount that the concentration of the substrate is preferably in the range from 0.01 to 1.0 mol/L, and more preferably from 0.1 to 0.5 mol/L.

The reaction temperature is appropriately selected depending on the type of the solvent and the like, but is preferably in the range from −10° C. to 100° C., and more preferably from 0° C. to 50° C., from the viewpoint of the reaction efficiency.

The atmosphere inside the reaction system may be air, inert gas, or the like.

After completion of the reaction, the product may optionally be subjected to a normal post-treatment (e.g., removal of the solvent, washing of the product, and chromatographic separation).

The embodiments of the present invention can improve the yield of the spirolactone calculated based on the molar quantity of the carboxyl group-containing aromatic compound (substrate) to 20% or higher. The yield can preferably be improved to 40% or higher (particularly preferably 50% or higher).

It is possible to achieve excellent enantioselectivity by utilizing the N-spiro quaternary ammonium salt represented by the general formula (2) as the quaternary ammonium salt, so that the enantioselectivity can preferably be improved to 50% or higher (more preferably 70% or higher, and particularly preferably 80% or higher).

The embodiments of the present invention thus make it possible to efficiently produce an aromatic compound having a ring structure that includes a nitrogen atom or an oxygen atom by subjecting the substrate to an intramolecular cyclization reaction without requiring multi-stage reactions.

EXAMPLES

The invention is further described below by way of examples. Note that the invention is not limited to the following examples.

1. Compound Analysis Method
(1) $^1$H-NMR Spectrum and $^{13}$C-NMR Spectrum $^1$H-NMR spectrum and $^{13}$C-NMR spectrum were measured at 400 MHz and 100 MHz, respectively, using a nuclear magnetic resonance spectrometer "ECS-400" (manufactured by JEOL Ltd.).

(2) IR Analysis

IR analysis was performed using a Fourier transform infrared spectrophotometer "FT/IR 460 Plus" (manufactured by JASCO Corporation).

(3) Mass Spectrometry

Mass spectrometry was performed using a high-performance double-focusing mass spectrometer "JMS-700" (manufactured by JEOL Ltd.).

(4) Enantioselectivity (% ee)

The enantioselectivity was measured using a high-performance liquid chromatographic system "LC-10" (manufactured by Shimadzu Corporation) and a chiral column "DAICEL CHIRALPAK AD-H", "DAICEL CHIRALPAK AS-H", "DAICEL CHIRALPAK AS-3", "DAICEL CHIRALPAK IA", or "DAICEL CHIRALCEL OD-H" (manufactured by Daicel Corporation). The size of each column is 4.6 mm (diameter)$_{x250}$ mm. The column and mobile phase used are described together with the NMR analysis data or the like.

2. Quaternary Ammonium Salt

The quaternary ammonium salts other than tetrabutylammonium iodide ($Bu_4N^+I^-$) were synthesized in accordance with a method by M. Uyanik, H. Okamoto, T. Yasui, and K. Ishihara, Science 328 (2010) 1376.

3. Production of 2-Acylindoline

An aniline derivative (an) was used as a substrate (raw material) for producing a 2-acylindoline. The aniline derivative (an) and an acylindoline compound (ai) (i.e., a raw material for producing the aniline derivative (an)) were synthesized as described below. The reaction was monitored by thin-layer chromatography (TLC) using a TLC plate "Pre-coated TLC plate" (silica gel 60 GF254, 0.25 mm) manufactured by Merck.

3-1. Synthesis of Acylindolyl Compound

Synthesis Example 1

Synthesis of Dihydroquinoline Compound Having Tert-Butoxycarbonyl Group

A dihydroquinoline compound (ai1) having a tert-butoxycarbonyl group (Boc group) (i.e., tert-butyl 2-oxo-3,4-dihydroquinoline-1(2H)-carboxylate) was produced from 3,4-dihydroquinolin-2(1H)-one (raw material (aa)) by the following method (see scheme (1-1)).

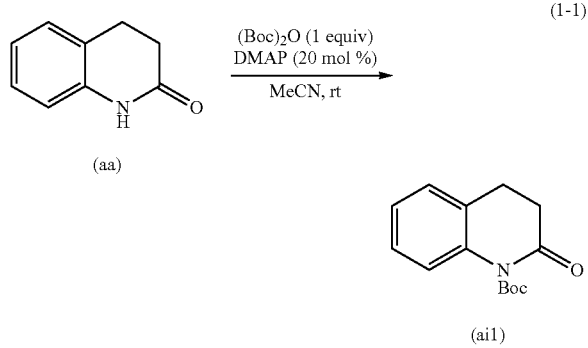

A reactor was charged with 1.5 g (10 mmol) of 3,4-dihydroquinolin-2(1H)-one and 56 mL of acetonitrile (MeCN) as a solvent, and 2.3 mL (10 mmol) of di-tert-butyl dicarbonate ((Boc)$_2$O) and 0.24 g (2 mmol) of N,N-dimethyl-4-aminopyridine (DMAP) were added dropwise to the mixture. Subsequently, the mixture was reacted at room temperature (about 20° C.) for 12 hours with stirring. The resulting reaction product was then washed with water, and extracted with ethyl acetate. After the addition of excess anhydrous magnesium sulfate to the resulting organic layer, the solvent was evaporated under reduced pressure to obtain a concentrate including a crude product. The concentrate was subjected to silica gel flash column chromatography (eluant: hexane/ethyl acetate=3/1) to obtain tert-butyl 2-oxo-3,4-dihydroquinoline-1(2H)-carboxylate (yellow oily product) represented by the formula (ai1) having a Boc group (($CH_3$)$_3$COC(O)—) as a protecting group (yield: 99%). The analysis data for the resulting compound (ai1) is shown below.

tert-Butyl 2-oxo-3,4-dihydroquinoline-1(2H)-carboxylate:
TLC (hexane:EtOAc=3:1) R$_f$ 0.56
$^1$H NMR (CDCl$_3$, 400 MHz) δ 1.60 (s, 9H), 2.63 (t, J=7.3 Hz, 2H), 2.92 (t, J=7.3 Hz, 2H), 6.94 (d, J=8.2 Hz, 1H), 7.04 (t, J=7.8 Hz, 1H), 7.16 (d, J=7.8 Hz, 1H), 7.20 (t, J=8.2 Hz, 1H)
$^{13}$C NMR (CDCl$_3$, 100 MHz) δ 25.2, 27.4, 32.0, 84.7, 116.6, 123.9, 125.6, 127.1, 127.8, 136.8, 151.5, 169.0.

In Synthesis Examples 2 to 4, dihydroquinoline compounds (ai2) to (ai4) in which a functional group derived from acyl chloride is bonded to a nitrogen atom as a protecting group were produced from 3,4-dihydroquinolin-2(1H)-one (raw material (aa)) (see scheme (1-2)).

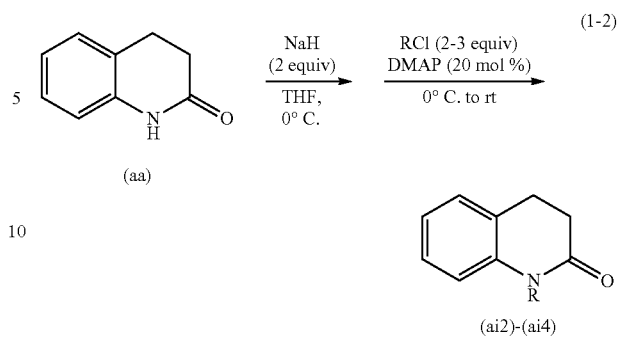

Synthesis Example 2

Synthesis of Dihydroquinoline Compound Having Benzyloxycarbonyl Group

A reactor was charged with 1.5 g (10 mmol) of 3,4-dihydroquinolin-2(1H)-one and 77 mL of tetrahydrofuran as a solvent. After cooling the mixture to 0° C., 0.8 g (20 mmol) of sodium hydride was added dropwise to the mixture. The mixture was stirred for 30 minutes, and held at 0° C., followed by the addition of 5.12 g (30 mmol) of benzyl chloroformate (acyl chloride (RCl)) and 0.24 g (2 mmol) of N,N-dimethyl-4-aminopyridine (DMAP). After adjusting the temperature of the reaction system to room temperature (about 20° C.), the mixture was reacted for 12 hours with stirring. After cooling the mixture including the reaction product to 0° C., water was added dropwise to the mixture, followed by extraction with ethyl acetate. After the addition of excess anhydrous magnesium sulfate to the resulting organic layer, the solvent was evaporated under reduced pressure to obtain a concentrate including a crude product. The concentrate was subjected to silica gel flash column chromatography (eluant: hexane/ethyl acetate=1/1) to obtain benzyl 2-oxo-3,4-dihydroquinoline-1(2H)-carboxylate (yellow oily product) represented by the following formula (ai2) having a Cbz group (PhCH$_2$OCO—) as a protecting group (yield: 76%). The analysis data for the resulting compound (ai2) is shown below.

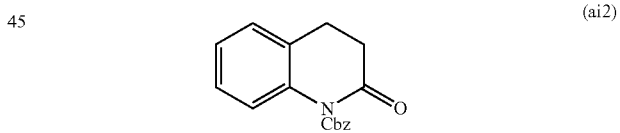

Benzyl 2-oxo-3,4-dihydroquinoline-1(2H)-carboxylate:
TLC (hexane:EtOAc=1:1) R$_f$=0.58
$^1$H NMR (CDCl$_3$, 400 MHz) δ 2.69 (t, J=6.9 Hz, 2H), 2.94 (t, J=6.9 Hz, 2H), 5.40 (s, 2H), 6.90 (d, J=7.8 Hz, 1H), 7.06 (t, J=7.3 Hz, 1H), 7.16 (t, J=7.3 Hz, 2H), 7.31-7.40 (m, 3H), 7.16 (d, J=7.8 Hz, 2H)
$^{13}$C NMR (CDCl$_3$, 100 MHz) δ 25.3, 32.8, 69.8, 118.4, 124.6, 126.8, 127.2, 127.8, 128.5, 128.6, 128.7, 134.3, 136.7, 153.3, 169.7.

Synthesis Example 3

Synthesis of Dihydroquinoline Compound Having Methanesulfonyl Group 1-(Methylsulfonyl)-3,4-dihydroquinolin-1(2H)-one (white solid) represented by the following formula (ai3) having an Ms group (CH₃SO₄—) as a protecting group was obtained in the same manner as in Synthesis Example 2, except that methanesulfonyl chloride (2.29 g, 20 mmol) was used as the acyl chloride (RCl) instead of benzyl chloroformate (yield: 28%). The analysis data for the resulting compound (ai3) is shown below.

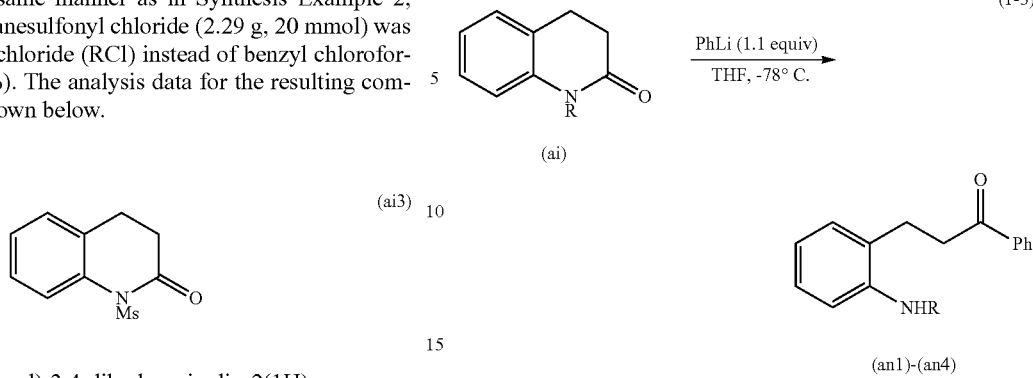

1-(Methylsulfonyl)-3,4-dihydroquinolin-2(1H)-one:

TLC (hexane:EtOAc=1:1) $R_f$=0.35

$^1$H NMR (CDCl₃, 400 MHz) δ 2.73 (t, J=6.6 Hz, 2H), 2.92 (t, J=6.6 Hz, 2H), 3.56 (s, 3H), 7.18 (t, J=7.3 Hz, 1H), 7.23 (d, J=7.3 Hz, 1H), 7.28 (t, J=8.2 Hz, 1H), 7.45 (d, J=8.2 Hz, 1H)

$^{13}$C NMR (CDCl₃, 100 MHz) δ 25.3, 35.3, 44.0, 122.5, 126.1, 127.1, 127.6, 130.2, 135.2, 173.2.

Synthesis Example 4

Synthesis of Dihydroquinoline Compound Having Protecting Group (Troc)

2,2,2-Trichloroethyl 2-oxo-3,4-dihydroquinoline-1(2H)-carboxylate (white solid) represented by the following formula (ai4) having a Troc group (Cl₃CCH₂OCO—) as a protecting group was obtained in the same manner as in Synthesis Example 2, except that methanesulfonyl chloride (6.36 g, 30 mmol) was used as the acyl chloride (RCl) instead of benzyl chloroformate (yield: 78%). The analysis data for the resulting compound (ai4) is shown below.

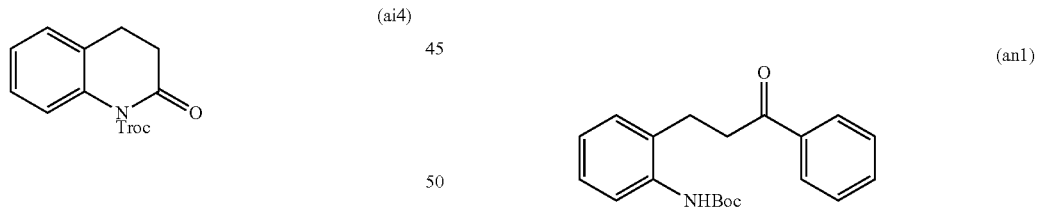

2,2,2-Trichloroethyl 2-oxo-3,4-dihydroquinoline-1(2H)-carboxylate

TLC (hexane:EtOAc=1:1) $R_f$=0.61

$^1$H NMR (CDCl₃, 400 MHz) δ 2.75 (t, J=6.4 Hz, 2H), 2.99 (t, J=6.4 Hz, 2H), 4.99 (s, 2H), 7.12-7.16 (m, 2H), 7.22-7.27 (m, 2H)

$^{13}$C NMR (CDCl₃, 100 MHz) δ 25.2, 33.4, 76.1, 93.8, 76.1, 93.8, 120.2, 125.2, 127.1, 127.6, 127.8, 136.1, 151.6, 170.0.

3-2. Synthesis of Aniline Derivative (an) (1)

In Synthesis Examples 5 to 8, aniline derivatives (an1) to (an4) were produced from the acylindolyl compounds (ai1) to (ai4) obtained in Synthesis Examples 1 to 4 (see scheme (1-3)).

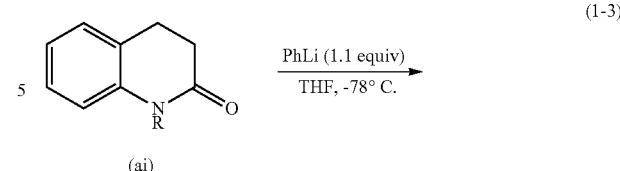

Synthesis Example 5

Synthesis of Aniline Derivative (an1)

A reactor was charged with 2 mmol of tert-butyl 2-oxo-3,4-dihydroquinoline-1(2H)-carboxylate (ai1) obtained in Synthesis Example 1 and 6.9 mL of tetrahydrofuran as a solvent to prepare a solution. After cooling the solution to −78° C. using dry ice, 2.0 mL (1.1 M, 2.2 mmol) of phenyllithium (PhLi) was slowly added dropwise to the solution. The mixture was reacted at −78° C. for 7 hours with stirring. The mixture including the reaction product was added to an ammonium chloride aqueous solution (5 mL), and the mixture was stirred. The mixture was extracted twice with ethyl acetate, and the reaction product was washed with a sodium chloride solution. After the addition of excess anhydrous magnesium sulfate to the collected organic layer, the solvent was evaporated under reduced pressure to obtain a concentrate including a crude product. The concentrate was subjected to silica gel flash column chromatography (eluant: hexane/ethyl acetate=6/1) to obtain tert-butyl 2-(3-oxo-3-phenylpropyl)phenylcarbamate (white solid) represented by the following formula (an1) (yield: 78%). The analysis data for the resulting aniline derivative (an1) is shown below.

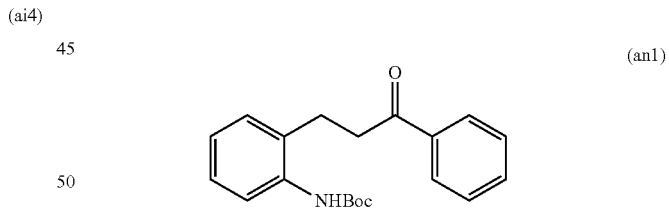

tert-Butyl 2-(3-oxo-3-phenylpropyl)phenylcarbamate

TLC (hexane:EtOAc=6:1) $R_f$=0.33

IR (KBr) 3401, 2980, 2931, 1729, 1677, 1508, 1440, 1231, 1148 cm$^{-1}$ $^1$H NMR (CDCl₃, 400 MHz) δ 1.54 (s, 9H), 3.01 (t, J=6.9 Hz, 2H), 3.37 (t, J=6.9 Hz, 2H), 7.03 (t, J=7.4 Hz, 1H), 7.16-7.20 (m, 2H), 7.74 (t, J=7.8 Hz, 2H), 7.53-7.57 (m, 2H), 7.71 (d, J=7.8 Hz, 1H), 7.95 (d, J=7.4 Hz, 2H)

$^{13}$C NMR (CDCl₃, 100 MHz) δ 24.4, 28.4, 39.6, 80.1, 123.3, 124.2, 127.0, 128.1, 128.6, 129.4, 132.0, 133.4, 136.1, 136.5, 153.8, 199.9

HRMS (FAB) m/z calcd for C₂₀H₂₄NO₃ (M+H) 326.1756. found 326.1718.

Synthesis Example 6

Synthesis of Aniline Derivative (an2)

Benzyl 2-(3-oxo-3-phenylpropyl)phenylcarbamate (white solid) represented by the following formula (an2) was obtained in the same manner as in Synthesis Example 5, except that 2 mmol of benzyl 2-oxo-3,4-dihydroquinoline-1(2H)-carboxylate (ai2) obtained in Synthesis Example 2 was used instead of tert-butyl 2-oxo-3,4-dihydroquinoline-1(2H)-carboxylate (ai1) (yield: 37%). The analysis data for the resulting aniline derivative (an2) is shown below.

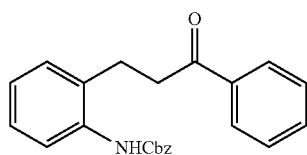

(an2)

Benzyl 2-(3-oxo-3-phenylpropyl)phenylcarbamate

TLC (hexane:EtOAc=6:1) $R_f$=0.23
IR (KBr) 3328, 3066, 2947, 1701, 1532, 1455, 1298, 1233 cm$^{-1}$
$^1$H NMR (CDCl$_3$, 400 MHz) δ 1.60 (s, 9H), 2.63 (t, J=7.3 Hz, 2H), 2.92 (t, J=7.3 Hz, 2H), 6.94 (d, J=8.2 Hz, 1H), 7.04 (t, J=7.8 Hz, 1H), 7.16 (d, J=7.8 Hz, 1H), 7.20 (t, J=8.2 Hz, 1H)
$^{13}$C NMR (CDCl$_3$, 100 MHz) δ 24.1, 39.7, 66.6, 123.1, 124.5, 126.9, 127.9, 128.0, 128.1, 128.4, 128.5, 129.6, 132.2, 133.3, 135.6, 136.2, 136.4, 154.4, 199.9
HRMS (FAB) m/z calcd for C$_{23}$H$_{22}$NO$_3$ (M+H) 360.1600. found 360.1610.

Synthesis Example 7

Synthesis of Aniline Derivative (an3)

N-(2-(3-oxo-3-phenylpropyl)phenyl)methanesulfonamide (white solid) represented by the following formula (an3) was obtained in the same manner as in Synthesis Example 5, except that 2 mmol of 1-(methylsulfonyl)-3,4-dihydroquinolin-1(2H)-one (ai3) obtained in Synthesis Example 3 was used instead of tert-butyl 2-oxo-3,4-dihydroquinoline-1(2H)-carboxylate (ai1) (yield: 13%). The analysis data for the resulting aniline derivative (an3) is shown below.

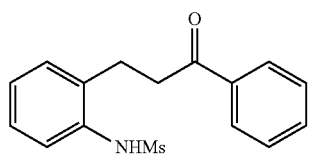

(an3)

N-(2-(3-Oxo-3-phenylpropyl)phenyl)methanesulfonamide

TLC (hexane:EtOAc=1:1) $R_f$=0.42
IR (KBr) 3266, 1675, 1492, 1328, 1150 cm$^{-1}$
$^1$H NMR (CDCl$_3$, 400 MHz) δ 3.07 (s, 3H), 3.08 (t, J=6.0 Hz, 2H), 3.47 (t, J=6.0 Hz, 2H), 7.15 (dt, J=1.4, 7.4 Hz, 1H), 7.23 (dq, J=1.4, 7.8 Hz, 2H), 7.47 (t, J=7.4 Hz, 2H), 7.55-7.59 (m, 1H), 7.95 (dd, J=1.4, 8.2 Hz, 2H), 8.61 (s, 1H)
$^{13}$C NMR (CDCl$_3$, 100 MHz) δ 24.1, 40.4, 40.3, 124.1, 126.1, 127.5, 128.2, 128.6, 130.4, 133.7, 134.3, 135.0, 135.9, 200.3
HRMS (FAB) m/z calcd for C$_{16}$H$_{18}$NO$_3$S (M+H) 304.1007. found 304.1014.

Synthesis Example 8

Synthesis of Aniline Derivative (an4))

2,2,2-Trichloroethyl 2-(3-oxo-3-phenylpropyl)phenylcarbamate (white solid) represented by the following formula (an4) was obtained in the same manner as in Synthesis Example 5, except that 2 mmol of 2,2,2-trichloroethyl 2-oxo-3,4-dihydroquinoline-1(2H)-carboxylate (ai4) obtained in Synthesis Example 3 was used instead of tert-butyl 2-oxo-3,4-dihydroquinoline-1(2H)-carboxylate (ai1) (yield: 11%). The analysis data for the resulting aniline derivative (an4) is shown below.

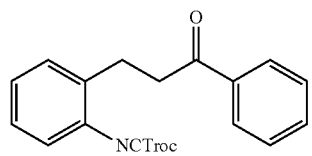

(an4)

2,2,2-Trichloroethyl 2-(3-oxo-3-phenylpropyl)phenylcarbamate

TLC (hexane:EtOAc=6:1) $R_f$=0.26
IR (KBr) 3301, 3028, 2956, 1738, 1682, 1524, 1450, 1223 cm$^{-1}$
$^1$H NMR (CDCl$_3$, 400 MHz) δ 3.05 (t, J=6.2 Hz, 2H), 3.43 (t, J=6.2 Hz, 2H), 4.89 (s, 2H), 7.10 (dt, J=1.1, 6.9 Hz, 1H), 7.20-7.24 (m, 2H), 7.44 (dt, J=1.8, 6.9 Hz, 2H), 7.56 (tt, J=1.8, 7.3 Hz, 1H), 7.71 (d, J=5.5 Hz, 1H), 7.94-7.96 (m, 2H), 8.65 (s, 1H)
$^{13}$C NMR (CDCl$_3$, 125 MHz) δ 24.1, 40.0, 74.4, 95.6, 123.4, 125.2, 127.1, 128.1, 128.6, 129.8, 132.8, 133.6, 135.1, 136.2, 152.9, 200.2
HRMS (FAB) m/z calcd for C$_{18}$H$_{17}$NO$_3$Cl (M+H) 400.0274. found 400.0231.

3-3. Synthesis of Aniline Derivative (an) (2)

In Synthesis Examples 9 to 12, aniline derivatives (an5) to (an8) were produced from the acylindolyl compounds (ai1) or (ai2) obtained in Synthesis Example 1 or 2 (see scheme (1-4)).

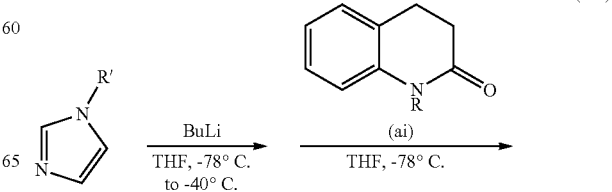

(1-4)

-continued

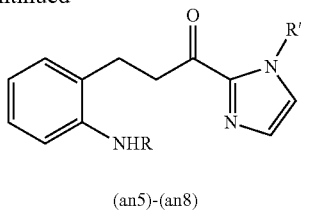

(an5)-(an8)

Synthesis Example 9

Synthesis of Aniline Derivative (an5)

A reactor was charged with 2.0 mmol of 1-arylimidazole and 11.1 mL of tetrahydrofuran as a solvent to prepare a solution. After cooling the solution to −78° C. using dry ice, 1.4 mL of a 1.6 M hexane solution containing 2.2 mmol of n-butyllithium (n-BuLi) was added to the solution, and the mixture was stirred. After removing the dry ice to adjust the temperature of the reaction system to −40° C., the mixture was stirred for 3 hours. The mixture was then cooled to −78° C. After the addition of a solution prepared by dissolving 2 mmol of tert-butyl 2-oxo-3,4-dihydroquinoline-1(2H)-carboxylate (ai1) obtained in Synthesis Example 1 in 4.0 mL of tetrahydrofuran using a cannula, the mixture was reacted at −78° C. with stirring. When 6 hours had elapsed, the reaction was terminated by adding a 1 N hydrochloric acid aqueous solution. The reaction product included in the reaction mixture was extracted with ethyl acetate. After the addition of excess anhydrous sodium sulfate to the collected organic layer, the solvent was evaporated under reduced pressure to obtain a concentrate including a crude product. The concentrate was subjected to silica gel flash column chromatography (eluant: hexane/ethyl acetate=1/1) to obtain tert-butyl 2-(3-oxo-3-(1-phenyl-1H-imidazol-2-yl)propyl)phenylcarbamate (white solid) represented by the following formula (an5) (yield: 88%). The analysis data for the resulting aniline derivative (an5) is shown below.

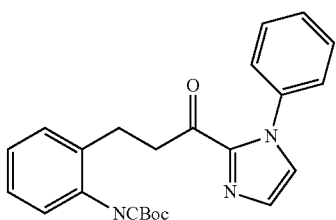

(an5)

tert-Butyl 2-(3-oxo-3-(1-phenyl-1H-imidazol-2-yl)propyl)phenylcarbamate

TLC (hexane:EtOAc=1:1) $R_f$=0.50
IR (KBr) 3240, 3129, 2972, 1717, 1684, 1400, 1157 cm$^{-1}$
$^1$H NMR (CDCl$_3$, 400 MHz) δ 1.56 (s, 9H), 3.01 (t, J=7.8 Hz, 2H), 3.27 (t, J=7.8 Hz, 2H), 6.99 (dt, J=1.4, 7.3 Hz, 1H), 7.16 (dd, J=1.4, 7.2 Hz, 1H), 7.19-7.23 (m, 2H), 7.28-7.31 (m, 2H), 7.38 (d, J=0.9 Hz, 1H), 7.48 (t, J=2.8 Hz, 3H), 7.96 (d, J=7.3 Hz, 1H), 8.31 (s, 1H)
$^{13}$C NMR (CDCl$_3$, 100 MHz) δ 27.5, 28.5, 41.4, 80.0, 121.7, 123.3, 125.8, 126.9, 127.0, 128.8, 128.9, 129.4, 129.8, 130.2, 136.6, 138.0, 142.1, 153.8, 190.2

HRMS (FAB) m/z calcd for $C_{23}H_{26}N_3O_3$ (M+H) 392.1974. found 392.1949.

Synthesis Example 10

Synthesis of Aniline Derivative (an6)

Benzyl 2-(3-oxo-3-(1-phenyl-1H-imidazol-2-yl)propyl)phenylcarbamate (white solid) represented by the following formula (an6) was obtained in the same manner as in Synthesis Example 9, except that 2 mmol of benzyl 2-oxo-3,4-dihydroquinoline-1(2H)-carboxylate (ai2) obtained in Synthesis Example 2 was used instead of tert-butyl 2-oxo-3,4-dihydroquinoline-1(2H)-carboxylate (ai1) (yield: 27%). The analysis data for the resulting aniline derivative (an6) is shown below.

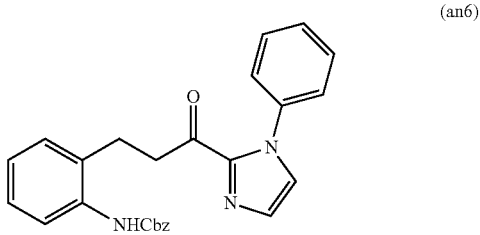 [SMILES: O=C(Nc1ccccc1CCC(=O)c1nccn1-c1ccccc1)OCc1ccccc1]

(an6)

Benzyl 2-(3-oxo-3-(1-phenyl-1H-imidazol-2-yl)propyl)phenylcarbamate

TLC (hexane:EtOAc=2:1) $R_f$=0.36
IR (KBr) 3232, 3107, 3033, 1725, 1686, 1594, 1549, 1453, 1402, 1227, 1211 cm$^{-1}$
$^1$H NMR (CDCl$_3$, 400 MHz) δ 3.04 (t, J=8.0 Hz, 2H), 3.16 (t, J=8.0 Hz, 2H), 5.27 (2, 2H), 6.99-7.03 (m, 2H), 7.07 (s, 1H), 7.16 (dd, J=1.4, 7.8 Hz, 1H), 7.23-7.27 (m, 3H), 7.34-7.48 (m, 8H), 8.07 (s, 1H), 9.30 (s, 1H)
$^{13}$C NMR (CDCl$_3$, 100 MHz) δ 28.3, 41.9, 66.8, 121.2, 123.4, 125.6, 125.7, 126.8, 127.2, 128.1, 128.4, 128.5, 129.5, 129.7, 154.4, 189.9

HRMS (FAB) m/z calcd for $C_{26}H_{24}N_3O_3$ (M+H) 426.1818. found 426.1839.

Synthesis Example 11

Synthesis of Aniline Derivative (an7)

tert-Butyl 2-(3-(1-(4-methoxyphenyl)-1H-imidazol-2-yl)-3-oxopropylphenyl)carbamate (white solid) represented by the following formula (an7) was obtained in the same manner as in Synthesis Example 9, except that 1-(4-methoxyphenyl)imidazole was used instead of 1-arylimidazole (yield: 59%). The analysis data for the resulting aniline derivative (an7) is shown below.

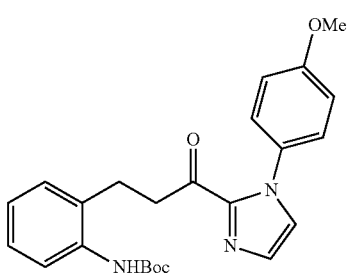

(an7)

tert-Butyl 2-(3-(1-(4-methoxyphenyl)-1H-imidazol-2-yl)-3-oxopropyl)phenylcarbamate TLC (hexane:EtOAc=2:1) $R_f$=0.29
IR (KBr) 3366, 2975, 1719, 1686, 1516, 1249, 1156 cm$^{-1}$
$^1$H NMR (CDCl$_3$, 400 MHz) δ 1.56 (s, 9H), 3.00 (t, J=7.8 Hz, 2H), 3.25 (t, J=7.8 Hz, 2H), 3.85 (s, 3H), 6.94-7.00 (m, 3H), 7.14-7.22 (m, 5H), 7.35 (s, 1H), 7.96 (d, J=6.4 Hz, 1H), 8.36 (s, 1H)
$^{13}$C NMR (CDCl$_3$, 100 MHz) δ 27.5, 28.5, 41.4, 55.4, 79.9, 114.0, 123.2, 126.9, 127.0, 127.2, 129.4, 129.6, 130.8, 136.5, 142.1, 153.8, 159.6, 190.2
HRMS (FAB) m/z calcd for C$_{24}$H$_{28}$N$_3$O$_4$ (M+H) 422.2080. found 422.2061.

Synthesis Example 12

Synthesis of Aniline Derivative (an8))

tert-Butyl 2-(3-oxo-3-(1-(4-trifluoromethyl)phenyl)-1H-imidazol-2-yl)propyl)phenylcarbamate (white solid) represented by the following formula (an8) was obtained in the same manner as in Synthesis Example 9, except that 1-(4-trifluoromethylphenyl)imidazole was used instead of 1-arylimidazole (yield: 38%). The analysis data for the resulting aniline derivative (an8) is shown below.

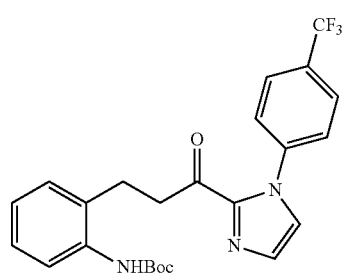

(an8)

tert-Butyl 2-(3-oxo-3-(1-(4-(trifluoromethyl)phenyl)-1H-imidazol-2-yl)propyl)phenylcarbamate TLC (hexane:EtOAc=1:1) $R_f$=0.411
IR (KBr) 3238, 2982, 1718, 1691, 1449, 1325, 1159, 1127 cm$^{-1}$
$^1$H NMR (CDCl$_3$, 400 MHz) δ 1.55 (s, 9H), 3.01 (t, J=7.7 Hz, 2H), 3.31 (t, J=7.7 Hz, 2H), 7.00 (dt, J=1.4, 7.3 Hz, 1H), 7.16 (dd, J=1.4, 7.3 Hz, 1H), 7.20-7.24 (m, 2H), 7.41-7.44 (m, 3H), 7.75 (d, J=8.2 Hz, 2H), 7.94 (d, J=5.6 Hz, 1H), 8.21 (s, 1H)
$^{13}$C NMR (CDCl$_3$, 100 MHz) δ 27.1, 28.4, 41.1, 79.9, 121.7, 122.1 (d, JC-F=4.8 Hz), 123.3, 126.1 (d, JC-F=2.9 Hz), 126.4, 126.7, 127.0, 129.4, 130.1, 130.3, 130.9 (d, JC-F=33 Hz), 136.4, 140.9, 141.9, 153.7, 190.4
HRMS (FAB) m/z calcd for C$_{24}$H$_{25}$N$_3$O$_3$F$_3$ (M+H) 460.1848. found 460.1888.

Synthesis Example 13

Synthesis of Aniline Derivative (an9)

tert-Butyl 2-(3-oxo-3-(1-(3,5-dimethoxy)phenyl)-1H-imidazol-2-yl)propyl)phenylcarbamate (white solid) represented by the following formula (an9) was obtained in the same manner as in Synthesis Example 9, except that 1-(3,5-dimethoxyphenyl)imidazole was used instead of 1-arylimidazole (yield: 67%). The analysis data for the resulting aniline derivative (an9) is shown below.

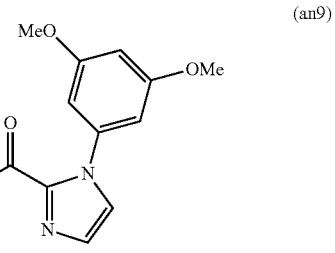

(an9)

tert-Butyl(2-(3-(1-(3,5-dimethoxyphenyl)-1H-imidazol-2-yl)-3-oxopropyl)phenyl)carbamate TLC (hexane:EtOAc=1:1) $R_f$=0.38
$^1$H NMR (CDCl$_3$, 400 MHz) δ 1.56 (s, 9H), 3.02 (t, J=7.8 Hz, 2H), 3.28 (t, J=7.8 Hz, 2H), 3.80 (s, 6H), 6.41 (s, 2H), 6.55 (s, 1H), 6.96 (t, J=7.3 Hz, 1H), 7.15-7.26 (m, 3H), 7.35 (s, 1H), 7.94-7.95 (m, 1H), 8.34 (s, 1H)

Synthesis Example 14

Synthesis of Aniline Derivative (an10)

tert-butyl 2-(3-oxo-3-(1-(4-dimethylamino)phenyl)-1H-imidazol-2-yl)propyl)phenylcarbamate (yellow solid) represented by the following formula (an10) was obtained in the same manner as in Synthesis Example 9, except that 1-(4-dimethylaminophenyl)imidazole was used instead of 1-arylimidazole (yield: 62%). The analysis data for the resulting aniline derivative (an10) is shown below.

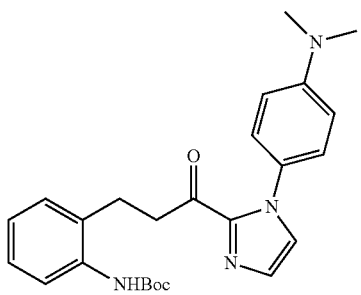

(an10)

tert-Butyl(2-(3-(1-(4-(dimethylamino)phenyl)-1H-imidazol-2-yl)-3-oxopropyl)phenyl)carbamate TLC (hexane:EtOAc=1:1) $R_f$=0.33

$^1$H NMR (CDCl$_3$, 400 MHz) δ 1.56 (s, 9H), 2.90-3.06 (m, 2H), 3.02 (s, 6H), 3.24 (t, J=7.8 Hz, 2H), 6.72 (dt, J=2.8, 9.2 Hz, 2H), 6.99 (dt, J=0.9, 7.3 Hz, 1H), 7.12-7.23 (m, 5H), 7.34 (s, 1H), 7.96-7.99 (m, 1H), 8.43 (s, 1H)

$^{13}$C NMR (CDCl$_3$, 100 MHz) δ 27.6, 28.5, 40.4, 41.5, 79.9, 111.6, 121.5, 123.1, 126.3, 126.7, 127.0, 127.4, 129.3, 129.4, 130.2, 136.6, 142.1, 150.3, 153.9, 190.1

Synthesis Example 15

Synthesis of Aniline Derivative (an11)

tert-Butyl 2-(3-oxo-3-(1-(naphthalen-1-yl)-1H-imidazol-2-yl)propyl)phenylcarbamate (white solid) represented by the following formula (an1) was obtained in the same manner as in Synthesis Example 9, except that 1-(naphthalen-1-yl)imidazole was used instead of 1-arylimidazole (yield: 72%). The analysis data for the resulting aniline derivative (an1) is shown below.

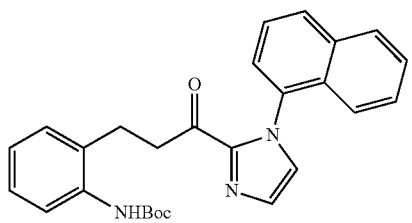

(an11)

tert-Butyl(2-(3-(1-(naphthalen-1-yl)-1H-imidazol-2-yl)-3-oxopropyl)phenyl)carbamate TLC (hexane:EtOAc=1:1) $R_f$=0.50

$^1$H NMR (CDCl$_3$, 400 MHz) δ 1.54 (s, 9H), 2.97 (t, J=7.8 Hz, 2H), 3.26 (t, J=7.8 Hz, 2H), 6.98 (t, J=7.6 Hz, 1H), 7.12 (d, J=7.6 Hz, 2H), 7.21 (t, J=7.1 Hz, 1H), 7.26 (s, 1H), 7.40-7.46 (m, 2H), 7.51 (s, 1H), 7.52-7.58 (m, 2H), 7.94-8.00 (m, 3H), 8.36 (s, 1H)

$^{13}$C NMR (CDCl$_3$, 100 MHz) δ 27.2, 28.4, 41.0, 79.9, 121.5, 123.2, 123.7, 124.9, 126.7, 127.0, 127.4, 127.5, 128.3, 129.3, 129.4, 129.7, 130.0, 133.8, 134.9, 136.4, 143.3, 153.7, 189.7

Synthesis Example 16

Synthesis of Aniline Derivative (an12)

tert-Butyl 2-(3-oxo-3-(1-(naphthalen-2-yl)-1H-imidazol-2-yl)propyl)phenylcarbamate (white solid) represented by the following formula (an12) was obtained in the same manner as in Synthesis Example 9, except that 1-(naphthalen-2-yl)imidazole was used instead of 1-arylimidazole (yield: 62%). The analysis data for the resulting aniline derivative (an12) is shown below.

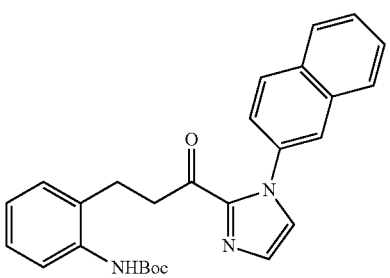

(an12)

tert-Butyl(2-(3-(1-(naphthalen-2-yl)-1H-imidazol-2-yl)-3-oxopropyl)phenyl)carbamate TLC (hexane:EtOAc=1:1) $R_f$=0.45

IR (KBr) 3277, 2975, 1721, 1686, 1447, 1402, 1238, 1157 cm$^{-1}$ $^1$H NMR (CDCl$_3$, 400 MHz) δ 1.52 (s, 9H), 3.01 (t, J=7.8 Hz, 2H), 3.29 (t, J=7.8 Hz, 2H), 6.97 (t, J=7.3 Hz, 1H), 7.14 (d, J=7.3 Hz, 1H), 7.18-7.23 (m, 2H), 7.34 (dd, J=1.8, 7.3 Hz, 1H), 7.40 (s, 1H), 7.48-7.58 (m, 2H), 7.73 (s, 1H), 7.82-8.00 (m, 4H), 8.36 (s, 1H)

$^{13}$C NMR (CDCl$_3$, 100 MHz) δ 27.4, 28.4, 41.3, 79.8, 121.6, 123.2, 123.8, 124.1, 126.9, 127.2, 127.8, 128.0, 128.7, 129.4, 129.8, 130.1, 132.7, 132.8, 135.4, 136.5, 142.1, 153.8, 190.2

HRMS (FAB) m/z calcd for C$_{27}$H$_{28}$N$_3$O$_3$ (M+H) 442.2131. found 442.2137.

3-4. Production and Evaluation (1) of 2-Acylindoline

In Examples 1-1 to 1-7, tert-butyl 2-benzoylindoline-1-carboxylate represented by the following formula (as1) was produced using the aniline derivative (an1) obtained in Synthesis Example 5 as a substrate, and using tetrabutylammonium iodide (Bu4N$^+$I$^-$) as a quaternary ammonium salt while changing types of the oxidizing agent, solvent, and the like and reaction conditions, and the yield was determined.

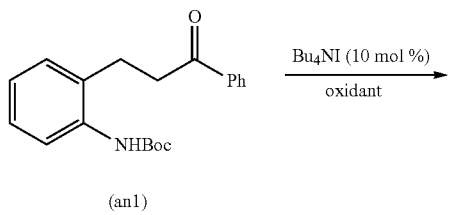

(an1)

-continued

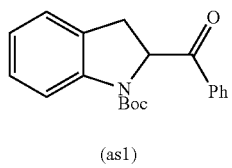

(as1)

Example 1-1

A reactor was charged with 325 mg (1.0 mmol) of tert-butyl 2-(3-oxo-3-phenylpropyl)phenylcarbamate (an11) obtained in Synthesis Example 5, 36.9 mg (0.10 mmol) of tetrabutylammonium iodide ($Bu_4N^+I^-$), and 50 mL of ethyl acetate as a solvent to prepare a solution. Subsequently, 364 μL of 5.5 M decane solution (manufactured by Aldrich) containing 2.0 mmol of tert-butyl hydroperoxide (TBHP) as an oxidizing agent was added to the solution in an amount corresponding to 2 equivalents based on the aniline derivative (an1). After adjusting the temperature of the reaction system to 50° C., the mixture was reacted for 10 hours with stirring. After cooling the reaction mixture including the reaction product to room temperature, the reaction mixture was added to 20 mL of water, and extracted twice with ethyl acetate. The resulting organic layer was sequentially washed with a saturated sodium sulfite ($Na_2SO_3$) aqueous solution, an NaCl aqueous solution, and water, followed by the addition of anhydrous sodium sulfate ($Na_2SO_4$). The solvent was then evaporated under reduced pressure to obtain a concentrate including a crude product. The concentrate was subjected to silica gel flash column chromatography (eluant: hexane/ethyl acetate=6/1) to obtain 246 mg (0.76 mmol) of tert-butyl 2-benzoylindoline-1-carboxylate represented by the formula (as1) (white solid). The yield was 76% (see Table 1-1). The analysis data for the resulting compound (as1) is shown below.

tert-Butyl 2-benzoylindoline-1-carboxylate

TLC (hexane:EtOAc=6:1) $R_f$=0.39
IR ($CHCl_3$) 3012, 2981, 1707, 1485, 1391, 1222, 1160 $cm^{-1}$
$^1$H NMR ($CDCl_3$, 400 MHz, mixture of two rotamers, *minor rotamer) δ 1.33 (s, 5H), 1.60*(s, 4H), 3.01-3.12 (m, 1H), 3.60-3.67 (m, 1H), 5.69 (dd, J=5.3, 11.7 Hz, 0.6H), 5.82-5.89*(m, 0.4H), 6.95 (t, J=7.3 Hz, 1H), 7.08 (t, J=7.3 Hz, 1H), 7.22-7.30 (m, 2H), 7.50 (t, J=7.5 Hz, 2H), 7.56-7.63 (m, 1H), 7.97 (t, J=8.9 Hz, 2H)
$^{13}$C NMR ($CDCl_3$, 100 MHz, mixture of two rotamers) δ 28.0, 28.4, 32.6, 32.7, 62.4, 63.1, 81.2, 82.2, 114.6, 122.3, 122.5, 124.5, 124.8, 127.6, 127.9, 128.1, 128.3, 128.7, 128.7, 128.8, 133.5, 134.2, 142.1, 143.0, 151.6, 152.6, 195.5, 196.2
HRMS (FAB) m/z calcd for $C_{20}H_{22}NO_3$ (M+H) 324.1600. found 324.1569.

Example 1-2 tert-Butyl 2-benzoylindoline-1-carboxylate represented by the formula (as1) was obtained in the same manner as in Example 1-1, except that hydrogen peroxide ($H_2O_2$) was used as an oxidizing agent instead of tert-butyl hydroperoxide (TBHP), tetrahydrofuran (THF) was used as a solvent instead of ethyl acetate, the reaction time was changed to 19 hours, and the reaction temperature was changed to room temperature (about 20° C.). The yield was 34% (see Table 1-1).

Example 1-3 tert-Butyl 2-benzoylindoline-1-carboxylate represented by the formula (as1) was obtained in the same manner as in Example 1-1, except that hydrogen peroxide ($H_2O_2$) was used as an oxidizing agent in an amount corresponding to 4 equivalents based on the aniline derivative (an1) instead of tert-butyl hydroperoxide (TBHP), diethyl ether ($Et_2O$) was used as a solvent instead of ethyl acetate, the reaction time was changed to 22 hours, and the reaction temperature was changed to room temperature (about 20° C.). The yield was 19% (see Table 1-1).

Example 1-4 tert-Butyl 2-benzoylindoline-1-carboxylate represented by the formula (as1) was obtained in the same manner as in Example 1-1, except that hydrogen peroxide ($H_2O_2$) was used as an oxidizing agent instead of tert-butyl hydroperoxide (TBHP), methyl tert-butyl ether ($^t$BuOMe) was used as a solvent instead of ethyl acetate, the reaction time was changed to 28 hours, and the reaction temperature was changed to room temperature (about 20° C.). The yield was 20% (see Table 1-1).

Example 1-5 tert-Butyl 2-benzoylindoline-1-carboxylate represented by the formula (as1) was obtained in the same manner as in Example 1-1, except that hydrogen peroxide ($H_2O_2$) was used as an oxidizing agent instead of tert-butyl hydroperoxide (TBHP), the reaction time was changed to 27 hours, and the reaction temperature was changed to room temperature (about 20° C.). The yield was 21% (see Table 1-1).

Example 1-6 tert-Butyl 2-benzoylindoline-1-carboxylate represented by the formula (as1) was obtained in the same manner as in Example 1-1, except that tetrahydrofuran (THF) was used as a solvent instead of ethyl acetate, the reaction time was changed to 5 hours, and the reaction temperature was changed to room temperature (about 20° C.). The yield was 69% (see Table 1-1).

Example 1-7 tert-Butyl 2-benzoylindoline-1-carboxylate represented by the formula (as1) was obtained in the same manner as in Example 1-1, except that the reaction time was changed to 102 hours, and the reaction temperature was changed to room temperature (about 20° C.). The yield was 39% (see Table 1-1).

TABLE 1-1

| Example | Substrate | Oxidizing agent | Solvent | Reaction tempereture, Time | Yield |
| --- | --- | --- | --- | --- | --- |
| 1-1 | (an1) | TBHP (2 equiv) | EtOAc | 50° C., 10 h | 76% |
| 1-2 | (an1) | $H_2O_2$ (2 equiv) | THF | RT, 19 h | 34% |
| 1-3 | (an1) | $H_2O_2$ (4 equiv) | EtOAc | RT, 22 h | 19% |

TABLE 1-1-continued

| Example | Substrate | Oxidizing agent | Solvent | Reaction tempereture, Time | Yield |
|---|---|---|---|---|---|
| 1-4 | (an1) | $H_2O_2$ (2 equiv) | $^t$BuOMe | RT, 28 h | 20% |
| 1-5 | (an1) | $H_2O_2$ (2 equiv) | EtOAc | RT, 27 h | 21% |
| 1-6 | (an1) | TBHP (2 equiv) | THF | RT, 5 h | 69% |
| 1-7 | (an1) | TBHP (2 equiv) | EtOAc | RT, 102 h | 39% |

3-5. Production and Evaluation of 2-Acylindoline (2)

In Examples 1-8 to 1-10, a 2-acylindoline was produced using the aniline derivatives (an2) to (an4) obtained in Synthesis Examples 6 to 8 as a substrate, and the yield was determined.

Example 1-8

A reactor was charged with 359 mg (1.0 mmol) of benzyl 2-(3-oxo-3-phenylpropyl)phenylcarbamate (an2) obtained in Synthesis Example 6, 36.9 mg (0.10 mmol) of tetrabutylammonium iodide ($Bu_4N^+I^-$), and 50 mL of ethyl acetate as a solvent to prepare a solution. Subsequently, 364 µL of 5.5 M decane solution (manufactured by Aldrich) containing 2.0 mmol of tert-butyl hydroperoxide (TBHP) as an oxidizing agent was added to the solution in an amount corresponding to 2 equivalents based on the aniline derivative (an2). After adjusting the temperature of the reaction system to room temperature (about 20° C.), the mixture was stirred for 5 hours, and then stirred (reacted) at 50° C. for 42 hours. After cooling the reaction mixture including the reaction product to room temperature, the reaction mixture was added to 20 mL of water, and extracted twice with ethyl acetate. The resulting organic layer was sequentially washed with a saturated sodium sulfite ($Na_2SO_3$) aqueous solution, an NaCl aqueous solution, and water, followed by the addition of anhydrous sodium sulfate ($Na_2SO_4$). The solvent was then evaporated under reduced pressure to obtain a concentrate including a crude product. The concentrate was subjected to silica gel flash column chromatography (eluant: hexane/ethyl acetate=6/1) to obtain benzyl 2-benzoylindoline-1-carboxylate (white solid) represented by the formula (as2). The yield was 10% (see Table 1-2). The analysis data for the resulting compound (as2) is shown below.

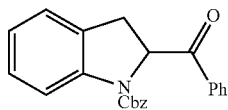

Benzyl 2-benzoylindoline-1-carboxylate

TLC (hexane:EtOAc=6:1) $R_f$=0.28
IR ($CHCl_3$) 3030, 3015, 1711, 1487, 1409, 1210 $cm^{-1}$
$^1$H NMR ($CDCl_3$, 400 MHz, mixture of two rotamers, *minor rotamer) δ 3.04-3.12 (m, 1H), 3.62-3.70 (m, 1H), 5.06-5.40 (m, 2H), 5.80 (dd, J=4.6, 11.9 Hz, 0.7H), 5.89*(dd, J=3.7, 12.7 Hz, 0.3H), 6.91-6.98 (m, 1H), 7.07 (d, J=7.3 Hz, 1H), 7.16-7.39 (m, 7H), 7.43-7.51 (m, 1H), 7.89 (d, J=7.3 Hz, 1H), 8.00-8.04 (m, 1H)
$^{13}$C NMR ($CDCl_3$, 100 MHz, mixture of two rotamers) δ 32.1, 32.9, 62.7, 62.8, 67.2, 68.1, 114.8, 114.9, 122.8, 122.9, 124.5, 124.9, 127.6, 127.7, 127.9, 128.6, 128.2, 128.3, 128.5, 128.6, 128.7, 128.8, 133.6, 133.9, 134.0, 135.7, 135.8, 141.6, 142.8, 195.2, 195.5

HRMS (FAB) m/z calcd for $C_{23}H_{20}NO_3$ (M+H) 358.1443. found 358.1443.

Example 1-9

A reactor was charged with 303 mg (1.0 mmol) of N-(2-(3-oxo-3-phenylpropyl)phenyl)methanesulfonamide (an3) obtained in Synthesis Example 7, 36.9 mg (0.10 mmol) of tetrabutylammonium iodide ($Bu_4N^+I^-$), and 50 mL of ethyl acetate as a solvent to prepare a solution. Subsequently, 364 µL of 5.5 M decane solution (manufactured by Aldrich) containing 2.0 mmol of tert-butyl hydroperoxide (TBHP) as an oxidizing agent was added to the solution in an amount corresponding to 2 equivalents based on the aniline derivative (an3). After adjusting the temperature of the reaction system to room temperature (about 20° C.), the mixture was stirred for 14 hours, and then stirred (reacted) at 50° C. for 4 hours. After cooling the reaction mixture including the reaction product to room temperature, the reaction mixture was added to 20 mL of water, and extracted twice with ethyl acetate. The resulting organic layer was sequentially washed with a saturated sodium sulfite ($Na_2SO_3$) aqueous solution, an NaCl aqueous solution, and water, followed by the addition of anhydrous sodium sulfate ($Na_2SO_4$). The solvent was then evaporated under reduced pressure to obtain a concentrate including a crude product. The concentrate was subjected to silica gel flash column chromatography (eluant: hexane/ethyl acetate=6/1) to obtain (1-(methylsulfonyl)indolin-2-yl)(phenyl)methanone (white solid) represented by the following formula (as3). The yield was 85% (see Table 1-2). The analysis data for the resulting compound (as3) is shown below.

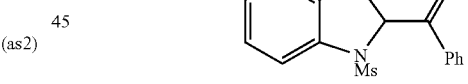

(1-(Methylsulfonyl)indolin-2-yl)(phenyl)methanone

TLC (hexane:EtOAc=1:1) $R_f$=0.55
IR ($CHCl_3$) 3030, 1699, 1482, 1348, 1155 $cm^{-1}$
$^1$H NMR ($CDCl_3$, 400 MHz) δ 3.13 (dd, J=4.6, 16.5 Hz, 1H), 3.30 (s, 3H), 3.75 (dd, J=11.9, 16.5 Hz, 1H), 6.00 (dd, J=4.6, 11.9 Hz, 1H), 6.98 (dt, J=0.9, 7.3 Hz, 1H), 7.11 (d, J=7.3 Hz, 1H), 7.23-7.30 (m, 2H), 7.52 (t, J=7.8 Hz, 1H), 7.52 (t, J=7.3 Hz, 1H), 7.97 (d, J=7.3 Hz, 2H)
$^{13}$C NMR ($CDCl_3$, 100 MHz) δ 33.4, 39.8, 65.5, 112.2, 122.9, 125.3, 128.3, 128.8, 129.0, 133.6, 134.0, 141.2, 195.5
HRMS (FAB) m/z calcd for $C_{16}H_{16}NO_3S$ (M+H) 302.0851. found 302.0842.

Example 1-10

A reactor was charged with 401 mg (0.10 mmol) of 2,2,2-trichloroethyl 2-(3-oxo-3-phenylpropyl)phenylcarbamate (an4) obtained in Synthesis Example 8, 36.9 mg (0.10 mmol) of tetrabutylammonium iodide (Bu$_4$N$^+$I$^-$), and 50 mL of ethyl acetate as a solvent to prepare a solution. Subsequently, 364 μL of 5.5 M decane solution (manufactured by Aldrich) containing 2.0 mmol of tert-butyl hydroperoxide (TBHP) as an oxidizing agent was added to the solution in an amount corresponding to 2 equivalents based on the aniline derivative (an4). After adjusting the temperature of the reaction system to room temperature (about 20° C.), the mixture was stirred for 5 hours, and then stirred (reacted) at 50° C. for 14 hours. After cooling the reaction mixture including the reaction product to room temperature, the reaction mixture was added to 20 mL of water, and extracted twice with ethyl acetate. The resulting organic layer was sequentially washed with a saturated sodium sulfite (Na$_2$SO$_3$) aqueous solution, an NaCl aqueous solution, and water, followed by the addition of anhydrous sodium sulfate (Na$_2$SO$_4$). The solvent was then evaporated under reduced pressure to obtain a concentrate including a crude product. The concentrate was subjected to silica gel flash column chromatography (eluant: hexane/ethyl acetate=6/1) to obtain 2,2,2-trichloroethyl 2-benzoylindoline-1-carboxylate (white solid) represented by the following formula (as4). The yield was 48% (see Table 1-2). The analysis data for the resulting compound (as4) is shown below.

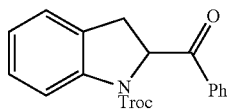

(as4)

2,2,2-Trichloroethyl 2-benzoylindoline-1-carboxylate

TLC (hexane:EtOAc=6:1), R$_f$=0.34
IR (CHCl$_3$) 3010, 2982, 1486, 1407, 1390 cm$^{-1}$
$^1$H NMR (CDCl$_3$, 400 MHz, mixture of two rotamers, *minor rotamer) δ 3.12 (dd, J=4.1, 16.5 Hz, 1H), 3.68-3.77 (m, 1H), 4.62 (d, J=11.9 Hz, 0.7H), 4.86 (d, J=11.9 Hz, 0.7H), 4.91*(d, J=11.9 Hz, 0.3H), 5.02*(d, J=11.9 Hz, 0.3H), 5.92* (dd, J=4.1, 11.9 Hz, 0.3H), 5.96 (dd, J=4.1, 11.9 Hz, 0.7H), 6.99-7.04 (m, 1H), 7.11 (d, J=7.3 Hz, 1H), 7.23-7.31 (m, 1H), 7.51 (t, J=7.4 Hz, 2H), 7.63 (t, J=7.4 Hz, 1H), 7.82*(d, J=8.2 Hz, 0.3H), 7.98-8.01 (m, 2.7H)
$^{13}$C NMR (CDCl$_3$, 100 MHz, mixture of two rotamers) δ 32.1, 32.8, 62.6, 63.0, 74.6, 75.7, 94.8, 114.9, 115.3, 123.4, 123.5, 124.6, 125.0, 127.8, 128.1, 128.3, 128.5, 128.6, 128.8, 133.6, 133.7, 150.2, 151.8, 194.5, 194.6
HRMS (FAB) m/z calcd for C$_{18}$H$_{15}$NO$_3$Cl$_3$ (M+H) 398.0118. found 398.0080.

TABLE 1-2

| Example | Substrate | Reaction tempereture, Time | Yield |
| --- | --- | --- | --- |
| 1-8 | (an2) | RT, 5 h → 50° C., 42 h | 10% |
| 1-9 | (an3) | RT, 14 h → 50° C., 4 h | 85% |
| 1-10 | (an4) | RT, 5 h → 50° C., 14 h | 48% |

3-6. Production and Evaluation of 2-Acylindoline (3)

In Examples 1-11 to 1-14, a 2-acylindoline was produced using the aniline derivative (an5) or (an6) obtained in Synthesis Example 9 or 10 as a substrate, and using a compound represented by the following general formula (25) wherein R$^5$ is 3,5-(3,5-(CF$_3$)$_2$C$_6$H$_3$)$_2$C$_6$H$_3$ or 4-(4-CF$_3$C$_6$H$_4$)C$_6$H$_4$, or a compound represented by the following general formula (26) wherein R$^5$ is 3,5-(3,5-(CF$_3$)$_2$C$_6$H$_3$)$_2$C$_6$H$_3$ or 4-(4-CF$_3$C$_6$H$_4$)C$_6$H$_4$, as a quaternary ammonium salt, and the yield was determined.

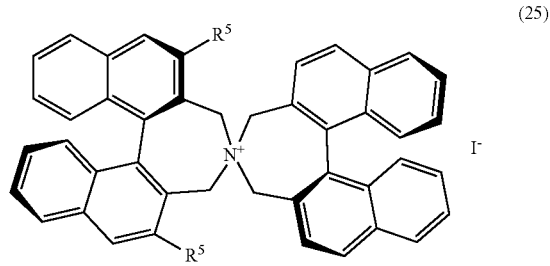

(25)

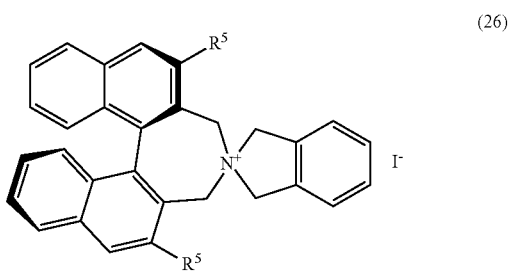

(26)

Example 1-11

A reactor was charged with 39.1 mg (0.1 mmol) of tert-butyl 2-(3-oxo-3-phenylpropyl)phenyl carbamate (an5) obtained in Synthesis Example 5, 17.2 mg (0.01 mmol) of the compound represented by the general formula (25) wherein R$^5$ is 3,5-(3,5-(CF$_3$)$_2$C$_6$H$_3$)$_2$C$_6$H$_3$ as a quaternary ammonium salt, and 5.0 mL of diethyl ether (Et$_2$O) as a solvent to prepare a solution. Subsequently, 364 μL of 5.5 M decane solution (manufactured by Aldrich) containing 2.0 mmol of tert-butyl hydroperoxide (TBHP) as an oxidizing agent was added to the solution in an amount corresponding to 2 equivalents based on the aniline derivative (an5). After adjusting the temperature of the reaction system to room temperature (about 20° C.), the mixture was reacted for 10 hours with stirring. The reaction mixture including the reaction product was added to 5 mL of water, and extracted twice with ethyl acetate. The resulting organic layer was sequentially washed with a saturated sodium sulfite (Na$_2$SO$_3$) aqueous solution, an NaCl aqueous solution, and water, followed by the addition of anhydrous sodium sulfate (Na$_2$SO$_4$). The solvent was then evaporated under reduced pressure to obtain a concentrate including a crude product. The concentrate was subjected to silica gel flash column chromatography (eluant: hexane/ethyl acetate=3/1) to obtain tert-butyl 2-(1-phenyl-1H-imidazole-2-carbonyl)indoline-1-carboxylate (white solid) represented by the following formula (as5). The yield was 89% (see Table 1-3). The analysis data for the resulting compound (as5) is shown below.

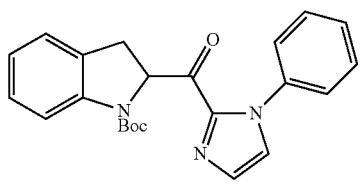

tert-Butyl 2-(1-phenyl-1H-imidazole-2-carbonyl)indoline-1-carboxylate

TLC (hexane:EtOAc=1:1), $R_f$=0.50
IR (CHCl$_3$) 3010, 2982, 1706, 1486, 1407, 1390 cm$^{-1}$
$^1$H NMR (CDCl$_3$, 400 MHz, mixture of two rotamers, *minor rotamer) δ 1.36 (s, 5H), 1.58*(s, 4H), 3.12 (dd, J=4.3, 16.7 Hz, 1H), 3.71 (dd, J=12.2, 16.7 Hz, 1H), 6.11-6.16 (m, 1H), 6.88 (t, J=7.3 Hz, 1H), 7.05 (d, J=6.4 Hz, 1H), 7.14-7.16 (m, 1H), 7.22-7.47 (m, 7.4H), 7.87 (d, J=7.8 Hz, 0.6H)
$^{13}$C NMR (CDCl$_3$, 100 MHz, mixture of two rotamers) δ 28.3, 28.4, 32.2, 32.9, 62.6, 80.6, 81.9, 114.4 (2C), 122.2, 124.2, 124.7, 125.7, 125.8, 127.1, 127.3, 127.5, 127.7, 128.0, 128.5, 128.6, 128.9 (2C), 129.1, 129.5, 130.0 (2C), 137.7, 140.7, 140.9, 142.3, 143.2, 151.5, 152.5, 186.8, 186.9
HRMS (FAB) m/z calcd for $C_{23}H_{24}N_3O_3$ (M+H) 390.1818. found 390.1791

Example 1-12 tert-Butyl-2-(1-phenyl-1H-imidazole-2-carbonyl)indoline-1-carboxylate (white solid) represented by the formula (as5) was obtained in the same manner as in Example 1-11, except that the compound represented by the general formula (26) wherein R$^5$ is 3,5-(CF$_3$)$_2$C$_6$H$_3$ was used as a quaternary ammonium salt in an amount of 9.5 mg (0.01 mmol), and the reaction time was changed to 24 hours. The yield was 43% (see Table 1-3).

Example 1-13

Benzyl-2-(1-phenyl-1H-imidazole-2-carbonyl)indoline-1-carboxylate (white solid) represented by the following formula (as6) was obtained in the same manner as in Example 1-11, except that tert-butyl-2-(3-oxo-3-phenylpropyl)phenyl carbamate (an6) obtained in Synthesis Example 10 was used as a substrate in an amount of 42.6 mg (0.1 mmol), and the reaction time was changed to 7 hours. The yield was 92% (see Table 1-3). The analysis data for the resulting compound (as6) is shown below.

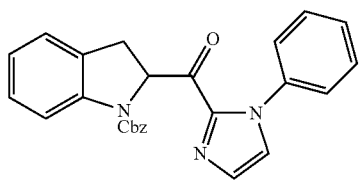

Benzyl 2-(1-phenyl-1H-imidazole-2-carbonyl)indoline-1-carboxylate

TLC (hexane:EtOAc=2:1), $R_f$=0.31
IR (KBr) 3031, 3012, 1708, 1487, 1409 cm$^{-1}$
$^1$H NMR (CDCl$_3$, 400 MHz, mixture of two rotamers, *minor rotamer) δ 3.18 (dd, J=4.1, 16.5 Hz, 1H), 3.78 (dd, J=11.4, 16.5 Hz, 1H), 5.10-5.37 (m, 2H), 6.22 (dd, J=4.1, 11.4 Hz, 1H), 6.93 (t, J=6.8 Hz, 1H), 7.00-7.02 (m, 2H), 7.08 (d, J=7.3 Hz, 1H), 7.16-7.46 (m, 12.4H), 7.92 (d, J=7.8 Hz, 0.6H)
$^{13}$C NMR (CDCl$_3$, 100 MHz, mixture of two rotamers) δ 32.7, 33.5, 62.8, 63.3, 67.0, 68.2, 114.5, 114.9, 122.7, 122.9, 125.8, 125.9, 127.5, 127.8, 127.9, 128.0, 128.3, 128.4, 128.7, 128.9, 129.0, 129.0, 129.2, 130.3, 136.0, 136.2, 137.7, 137.9, 140.6, 140.8, 143.0, 152.2, 153.6, 186.3, 186.5
HRMS (FAB) m/z calcd for $C_{26}H_{23}N_3O_3$(M+H) 424.1661. found 424.1673

Example 1-14

Benzyl-2-(1-phenyl-1H-imidazole-2-carbonyl)indoline-1-carboxylate (white solid) represented by the formula (as6) was obtained in the same manner as in Example 1-11, except that tert-butyl-2-(3-oxo-3-phenylpropyl)phenyl carbamate (an6) obtained in Synthesis Example 10 was used as a substrate in an amount of 42.6 mg (0.1 mmol), the compound represented by the general formula (26) wherein R$^5$ is 3,5-(CF$_3$)$_2$C$_6$H$_3$ was used as a quaternary ammonium salt in an amount of 9.5 mg (0.01 mmol), and the reaction time was changed to 24 hours. The yield was 15% (see Table 1-3).

TABLE 1-3

| Example | Substrate | Quaternary ammonium salt | Oxidizing agent | Yield |
| --- | --- | --- | --- | --- |
| 1-11 | (an5) | General formula (25)<br>R$^5$: 3,5-(3,5-(CF$_3$)$_2$C$_6$H$_3$)$_2$C$_6$H$_3$ | TBHP | 89% |
| 1-12 | (an5) | General formula (26)<br>R$^5$: 3,5-(CF$_3$)$_2$C$_6$H$_3$ | TBHP | 43% |
| 1-13 | (an6) | General formula (25)<br>R$^5$: 3,5-(3,5-(CF$_3$)$_2$C$_6$H$_3$)$_2$C$_6$H$_3$ | TBHP | 92% |
| 1-14 | (an6) | General formula (26)<br>R$^5$: 3,5-(CF$_3$)$_2$C$_6$H$_3$ | TBHP | 15% |

3-7. Production and Evaluation of 2-Acylindoline (4)

In Examples 1-15 to 1-27, tert-butyl-2-(1-phenyl-1H-imidazole-2-carbonyl)indoline-1-carboxylate (white solid) represented by the formula (as5) and benzyl-2-(1-phenyl-1H-imidazole-2-carbonyl)indoline-1-carboxylate (white solid) represented by the formula (as6) were produced using the aniline derivative (an5) or (an6) obtained in Synthesis Example 9 or 10 as a substrate, and using the compound represented by the general formula (25) wherein R$^5$ is -Ph (hereinafter referred to as "functional group A" or "A"), 3,5-(CF$_3$)$_2$C$_6$H$_3$ (hereinafter referred to as "functional group B" or "B"), 3,4,5-F$_3$C$_3$H$_3$ (hereinafter referred to as "functional group C" or "C"), 4-MeOC$_6$H$_5$ (hereinafter referred to as "functional group D" or "D"), 4-(CF$_3$)C$_6$H$_5$ (hereinafter referred to as "functional group E" or "E"), 4-[3,5-(CF$_3$)$_2$C$_6$H$_3$]C$_6$H$_4$ (hereinafter referred to as "functional group F" or "F"), or 4-(4-CF$_3$C$_6$H$_4$)C$_6$H$_4$ (hereinafter referred to as "functional group G" or "G"), as a quaternary ammonium salt, and the yield was determined.

HPLC measurement for determining the enantioselectivity of tert-butyl-2-(1-phenyl-1H-imidazole-2-carbonyl)indoline-1-carboxylate represented by the formula (as5) was performed using a chiral column "DAICEL CHIRALPAK AD-H" (eluant: hexane/ethanol=10/1, flow rate: 1 mL/min) (t$_1$=18 min, t$_2$=23 min).

On the other hand, HPLC measurement for determining the enantioselectivity of benzyl-2-(1-phenyl-1H-imidazole-2-carbonyl)indoline-1-carboxylate represented by the formula (as6) was performed using a chiral column "DAICEL

Example 1-15

A reactor was charged with 39.1 mg (0.1 mmol) of tert-butyl 2-(3-oxo-3-phenylpropyl)phenyl carbamate (an5) obtained in Synthesis Example 5, 0.01 mmol of the compound represented by the general formula (25) wherein $R^5$ is the functional group A as a quaternary ammonium salt, and 5.0 mL of diethyl ether ($Et_2O$) as a solvent to prepare a solution. Subsequently, 364 μL of 5.5 M decane solution (manufactured by Aldrich) containing 2.0 mmol of tert-butyl hydroperoxide (TBHP) as an oxidizing agent was added to the solution in an amount corresponding to 2 equivalents based on the aniline derivative (an5). After adjusting the temperature of the reaction system to room temperature (about 20° C.), the mixture was reacted for 10 hours with stirring. The reaction mixture including the reaction product was added to water (5 mL), and extracted twice with ethyl acetate. The resulting organic layer was sequentially washed with a saturated sodium sulfite ($Na_2SO_3$) aqueous solution, an NaCl aqueous solution, and water, followed by the addition of anhydrous sodium sulfate ($Na_2SO_4$). The solvent was then evaporated under reduced pressure to obtain a concentrate including a crude product. The concentrate was subjected to silica gel flash column chromatography (eluant: hexane/ethyl acetate=3/1) to obtain tert-butyl 2-(1-phenyl-1H-imidazole-2-carbonyl)indoline-1-carboxylate (white solid) represented by the formula (as5). The yield was 17%, and the enantioselectivity was 60% ee (see Table 1-4).

Examples 1-16 to 1-27 tert-Butyl-2-(1-phenyl-1H-imidazole-2-carbonyl)indoline-1-carboxylate represented by the formula (as5) and benzyl-2-(1-phenyl-1H-imidazole-2-carbonyl)indoline-1-carboxylate represented by the formula (as6) were obtained in the same manner as in Example 1-15, except that the aniline derivative (substrate), quaternary ammonium salt, and reaction time were changed as shown in Table 1-4. The yield and enantioselectivity are shown in Table 1-4.

Example 1-28 tert-Butyl-2-(1-(4-methoxyphenyl)-1H-imidazole-2-carbonyl)indoline-1-carboxylate (white solid) represented by the following formula (as7) was obtained in the same manner as in Example 1-15, except that tert-butyl-2-(3-(1-(4-methoxyphenyl)-1H-imidazol-2-yl)-3-oxopropylphenyl) carbamate (an7) obtained in Synthesis Example 11 was used as a substrate in an amount of 42.2 mg (0.1 mmol), the compound represented by the general formula (25) wherein $R^5$ is the functional group F was used as a quaternary ammonium salt in an amount of 12.8 mg (0.01 mmol), and the reaction time was changed to 11 hours. The yield was 94%, and the enantioselectivity determined by HPLC measurement (chiral column: "DAICEL CHIRALPAK AS-3", eluant: hexane/ethanol (=10/1), flow rate: 1 mL/min, $t_1$=24 min, $t_2$=29 min) was 78% ee (see Table 1-5). The analysis data for the resulting compound (as7) is shown below.

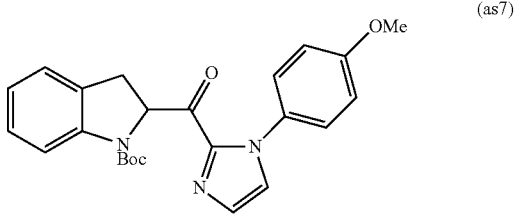 [SMILES: COc1ccc(-n2ccnc2C(=O)C2Cc3ccccc3N2C(=O)OC(C)(C)C)cc1]

(as7)

tert-Butyl 2-(1-(4-methoxyphenyl)-1H-imidazole-2-carbonyl)indoline-1-carboxylate TLC (hexane:EtOAc=2:1) $R_f$=0.24

IR ($CHCl_3$) 3011, 2981, 1706, 1517, 1485, 1390, 1252 $cm^{-1}$ $^1$H NMR ($CDCl_3$, 400 MHz, mixture of two rotamers, *minor rotamer) δ 1.36 (s, 8.1H), 3.11 (dd, J=4.6, 16.7 Hz, 1H), 3.70 (dd, J=11.4, 16.7 Hz, 1H), 3.82 (s, 2.7H), 3.88*(s, 0.3H), 6.09-6.16 (m, 1H), 6.87-6.91 (m, 3H), 6.99-7.06 (m, 1H), 7.13-7.35 (m, 5H), 7.76-8.08 (m, 1H), 6.47 (dd, J=7.8,

TABLE 1-4

| Example | Substrate | Quaternary ammonium salt | Oxidizing agent | Reaction time | Yield | Enantioselectivity |
|---|---|---|---|---|---|---|
| 1-15 | (an5) | $R^5$ of general formula (25): A | TBHP | 10 h | 17% | 60% |
| 1-16 | | $R^5$ of general formula (25): B | TBHP | 10 h | 65% | 20% |
| 1-17 | | $R^5$ of general formula (25): C | TBHP | 24 h | 99% | 47% |
| 1-18 | | $R^5$ of general formula (25): D | TBHP | 24 h | 99% | 55% |
| 1-19 | | $R^5$ of general formula (25): E | TBHP | 24 h | 95% | 65% |
| 1-20 | | $R^5$ of general formula (25): F | TBHP | 24 h | 99% | 69% |
| 1-21 | | $R^5$ of general formula (25): F | TBHP | 48 h | 72% | 79% |
| 1-22 | | $R^5$ of general formula (25): G | TBHP | 24 h | 74% | 68% |
| 1-23 | (an6) | $R^5$ of general formula (25): A | TBHP | 24 h | 87% | 38% |
| 1-24 | | $R^5$ of general formula (25): B | TBHP | 5 h | 89% | 46% |
| 1-25 | | $R^5$ of general formula (25): C | TBHP | 6 h | 38% | 62% |
| 1-26 | | $R^5$ of general formula (25): D | TBHP | 24 h | 49% | 70% |
| 1-27 | | $R^5$ of general formula (25): F | TBHP | 6 h | 44% | 60% |

3-8. Production and Evaluation of 2-Acylindoline (5)

In Examples 1-28 to 1-33, a 2-acylindoline was produced using the compounds (an7) to (an12) obtained in Synthesis Examples 11 to 16 as a substrate, and using the compound represented by the general formula (25) wherein $R_5$ is the functional group F as a quaternary ammonium salt, while changing reaction conditions.

11.0 Hz, 1H), 6.86 (t, J=7.3 Hz, 1H), 6.96 (d, J=8.2 Hz, 1H), 7.13-7.17 (m, 2H), 7.52 (dt, J=1.4, 6.2 Hz, 1H), 7.88 (dt, J=1.4, 7.8 Hz, 1H), 8.13 (dd, J=0.9, 7.8 Hz, 1H), 8.71-8.73 (m, 1H)

$^{13}$C NMR ($CDCl_3$, 100 MHz, mixture of two rotamers) δ 28.4, 28.6, 32.2, 32.9, 55.4, 62.6, 80.6. 81.9, 114.0, 114.4, 122.0, 122.1, 123.9, 124.2, 124.4, 124.7, 126.8, 127.0, 127.5, 127.6, 127.8, 128.0, 129.8, 129.9, 137.1, 137.2, 140.8, 140.9, 143.2, 143.8, 152.5, 152.7, 159.4, 159.7, 186.8

HRMS (FAB) m/z calcd for $C_{24}H_{26}N_3O_4$ (M+H) 420.1923. found 420.1926 $[\alpha]^{23}_D = -46.2$ (c 1.87, CHCl$_3$) for 78% ee.

Example 1-29 tert-Butyl-2-(1-(4-trifluoromethyl)phenyl)-1H-imidazole-2-carbonyl)indoline-1-carboxylate (white solid) represented by the following formula (as8) was obtained in the same manner as in Example 1-15, except that tert-butyl-2-(3-oxo-3-(1-(4-trifluoromethyl)phenyl)-1H-imidazol-2-yl)propyl)phenyl carbamate (an8) obtained in Synthesis Example 12 was used as a substrate in an amount of 46.0 mg (0.1 mmol), the compound represented by the general formula (25) wherein $R^5$ is the functional group F was used as a quaternary ammonium salt in an amount of 12.8 mg (0.01 mmol), and the reaction time was changed to 10 hours. The yield was 91%, and the enantioselectivity determined by HPLC measurement (chiral column: "DAICEL CHIRALPAK IA", eluant: hexane/ethanol (=10/1), flow rate: 1 mL/min, $t_1$=9 min, $t_2$=16 min) was 50% ee (see Table 1-5). The analysis data for the resulting compound (as8) is shown below.

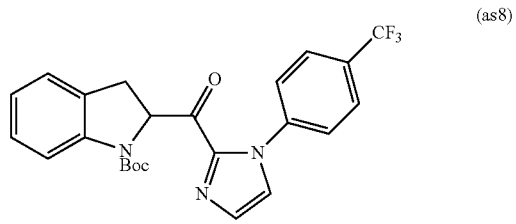 [SMILES: CC(C)(C)OC(=O)N1c2ccccc2CC1C(=O)c1nccn1-c1ccc(C(F)(F)F)cc1]

(as8)

tert-Butyl 2-(1-(4-(trifluoromethyl)phenyl)-1H-imidazole-2-carbonyl)indoline-1-carboxylate TLC (hexane:EtOAc=1:1) $R_f$=0.34
IR (CHCl$_3$) 3009, 2983, 1707, 1485, 1389, 1326 cm$^{-1}$
$^1$H NMR (CDCl$_3$, 400 MHz, mixture of two rotamers, *minor rotamer) δ 1.36 (s, 6.3H), 1.50*(s, 2.7H), 3.12 (dd, J=4.6, 16.9 Hz, 1H), 3.68-3.75 (m, 1H), 6.09-6.15 (m, 1H), 6.89 (t, J=7.8 Hz, 1H), 7.02-7.18 (m, 2H), 7.25-7.29 (m, 1H), 7.36-7.51 (m, 3H), 7.68 (dd, J=8.2, 16.8 Hz, 2H), 7.76-8.07 (m, 1H)
$^{13}$C NMR (CDCl$_3$, 100 MHz, mixture of two rotamers) δ 28.0, 28.3, 32.2, 32.9, 62.6, 80.7, 82.2, 114.3, 122.3 (d, JC-F=4 Hz), 123.9, 124.1, 124.3, 124.8, 126.2, 126.3, 126.5, 126.7, 127.1, 127.2, 127.7, 127.8, 130.6, 130.8, 137.3, 138.0, 140.6, 140.9, 141.4, 142.1, 143.1, 143.7, 152.6, 152.7, 187.2, 187.4
$^{19}$F NMR (CDCl$_3$, 376 MHz) δ -62.6
HRMS (FAB) m/z calcd for $C_{24}H_{23}O_3N_3F_3$ (M+H) 458.1692. found 458.1689
$[\alpha]^{24}_D = -29.4$ (c 1.88, CHCl$_3$) for 50% ee.

Example 1-30 tert-Butyl-2-(3-oxo-3-(1-(3,5-dimethoxy)phenyl)-1H-imidazole-2-carbonyl)indoline-1-carboxylate (white solid) represented by the following formula (as9) was obtained in the same manner as in Example 1-15, except that tert-butyl-2-(3-oxo-3-(1-(3,5-dimethoxy)phenyl)-1H-imidazol-2-yl)propyl)phenyl carbamate (an9) obtained in Synthesis Example 13 was used as a substrate in an amount of 22.6 mg (0.05 mmol), the compound represented by the general formula (25) wherein $R^5$ is the functional group F was used as a quaternary ammonium salt in an amount of 6.4 mg (0.005 mmol), and the reaction time was changed to 11 hours. The yield was 81%, and the enantioselectivity determined by HPLC measurement (chiral column: "DAICEL CHIRALPAK IA", eluant: hexane/ethanol (=10/1), flow rate: 1 mL/min, $t_1$=15 min, $t_2$=19 min) was 59% ee (see Table 1-5). The analysis data for the resulting compound (as9) is shown below.

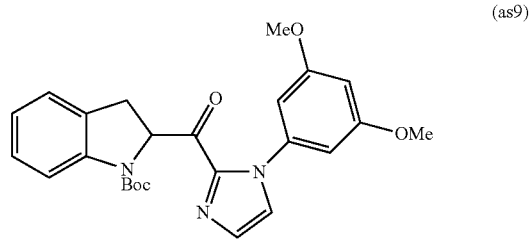 [SMILES: COc1cc(OC)cc(-n2ccnc2C(=O)C2Cc3ccccc3N2C(=O)OC(C)(C)C)c1]

(as9)

tert-Butyl 2-(1-(3,5-dimethoxyphenyl)-1H-imidazole-2-carbonyl)indoline-1-carboxylate TLC (hexane:EtOAc=2:1) $R_f$=0.27
$^1$H NMR (CDCl$_3$, 400 MHz, mixture of two rotamers, *minor rotamer) δ 1.37 (s, 5.4H), 1.58*(s, 3.6H), 3.12 (dd, J=4.1, 17.0 Hz, 1H), 3.68-3.75 (m, 1H), 3.76 (s, 6H, 6.09-6.13 (m, 1H), 6.39 (s, 1H), 6.45-6.50 (m, 2H), 6.89 (t, J=7.3 Hz, 1H), 7.05-7.07 (m, 1H), 7.11-7.18 (m, 1H), 7.23-7.34 (m, H), 7.47*(d, J=8.2 Hz, 0.4H), 7.88 (d, J=8.2 Hz, 0.6H)

Example 1-31 tert-Butyl-2-(1-(4-dimethylamino)phenyl)-1H-imidazole-2-carbonyl)indoline-1-carboxylate (white solid) represented by the following formula (as10) was obtained in the same manner as in Example 1-15, except that tert-butyl-2-(3-oxo-3-(1-(4-dimethylamino)phenyl)-1H-imidazol-2-yl)propyl)phenyl carbamate (an10) obtained in Synthesis Example 14 was used as a substrate in an amount of 21.7 mg (0.05 mmol), the compound represented by the general formula (25) wherein $R^5$ is the functional group F was used as a quaternary ammonium salt in an amount of 6.4 mg (0.005 mmol), and the reaction time was changed to 5 hours. The yield was 88%, and the enantioselectivity determined by HPLC measurement (chiral column: "DAICEL CHIRALPAK IA", eluant: hexane/ethanol (=10/1), flow rate: 1 mL/min, $t_1$=16 min, $t_2$=24 min) was 78% ee (see Table 1-5). The analysis data for the resulting compound (as10) is shown below.

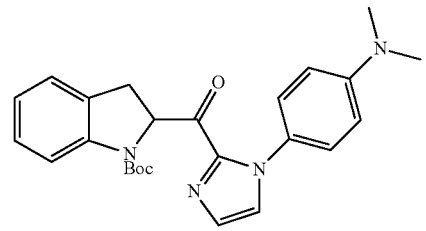

(as10)

tert-Butyl 2-(1-(4-(dimethylamino)phenyl)-1H-imidazole-2-carbonyl)indoline-1-carboxylate TLC (hexane:EtOAc=1:1) $R_f$=0.32
$^1$H NMR (CDCl$_3$, 400 MHz, mixture of two rotamers, *minor rotamer) δ 1.35 (s, 5.4H), 1.54*(s, 4.6H), 2.95-3.10 (m, 1H), 2.96 (s, 6H), 3.64-3.72 (m, 1H), 6.10-6.19 (m, 1H), 6.68-6.78 (m, 2H), 6.85-6.90 (m, 1H), 7.00-7.40 (m, 6H), 7.45*(d, J=8.2 Hz, 0.4H), 7.87 (d, J=7.8 Hz, 0.6H)

Example 1-32 tert-Butyl-2-(1-(naphthalen-1-yl)-1H-imidazole-2-carbonyl)indoline-1-carboxylate (white solid) represented by the following formula (as11) was obtained in the same manner as in Example 1-15, except that tert-butyl-2-(3-oxo-3-(1-(naphthalen-1-yl)-1H-imidazol-2-yl)propyl)phenyl carbamate (an11) obtained in Synthesis Example 15 was used as a substrate in an amount of 22.1 mg (0.05 mmol), the compound represented by the general formula (25) wherein R$^5$ is the functional group F was used as a quaternary ammonium salt in an amount of 6.4 mg (0.005 mmol), and the reaction time was changed to 8 hours. The yield was 90%, and the enantioselectivity determined by HPLC measurement (chiral column: "DAICEL CHIRALPAK IA" (×2), eluant: hexane/ethanol (=40/1), flow rate: 1 mL/min, $t_1$=65 min, $t_2$=75 min) was 68% ee (see Table 1-5). The analysis data for the resulting compound (as11) is shown below.

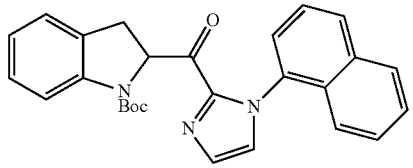

(as11)

tert-Butyl 2-(1-(naphthalen-1-yl)-1H-imidazole-2-carbonyl)indoline-1-carboxylate TLC (hexane:EtOAc=1:1) $R_f$=0.48
$^1$H NMR (CDCl$_3$, 400 MHz, mixture of four rotamers) δ 1.28, 1.36, 1.47, 1.53 (s, 9H for rotamers), 3.05-3.15 (m, 1H), 3.69-3.78 (m, 1H), 6.82-6.88 (m, 1H), 7.01-7.13 (m, 3H), 7.26-7.56 (m, 8H), 7.70-7.96 (m, 2H)

Example 1-33 tert-Butyl-2-(1-(naphthalen-2-yl)-1H-imidazole-2-carbonyl)indoline-1-carboxylate (white solid) represented by the following formula (as12) was obtained in the same manner as in Example 1-15, except that tert-butyl-2-(3-oxo-3-(1-(naphthalen-2-yl)-1H-imidazol-2-yl)propyl)phenyl carbamate (an12) obtained in Synthesis Example 16 was used as a substrate in an amount of 22.1 mg (0.05 mmol), the compound represented by the general formula (25) wherein R$^5$ is the functional group F was used as a quaternary ammonium salt in an amount of 6.4 mg (0.005 mmol), and the reaction time was changed to 22 hours. The yield was 74%, and the enantioselectivity determined by HPLC measurement (chiral column: "DAICEL CHIRALPAK IA", eluant: hexane/ethanol (=10/1), flow rate: 1 mL/min, $t_1$=13 min, $t_2$=42 min) was 66% ee (see Table 1-5). The analysis data for the resulting compound (as12) is shown below.

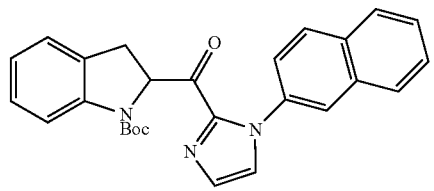

(as12)

tert-Butyl 2-(1-(naphthalen-2-yl)-1H-imidazole-2-carbonyl)indoline-1-carboxylate TLC (hexane:EtOAc=1:1) $R_f$=0.42
IR (CHCl$_3$) 3025, 2982, 1706, 1485, 1390, 1221, 1326 cm$^{-1}$
$^1$H NMR (CDCl$_3$, 400 MHz, mixture of two rotamers, *minor rotamer) δ 1.38 (s, 4.9H), 1.58*(s, 4.1H), 3.13-3.19 (m, 1H), 3.69-3.76 (m, 1H), 6.10-6.20 (m, 1H), 6.89 (t, J=7.1 Hz, 1H), 7.05-7.16 (m, 2H), 7.29-7.59 (m, 5H), 7.74-7.91 (m, 5H)
HRMS (FAB) m/z calcd for C$_{27}$H$_{26}$O$_3$N$_3$ (M+H) 440.1974. found 440.2014.

TABLE 1-5

| Example | Substrate | Reaction time | Yield | Enantioselectivity |
|---------|-----------|---------------|-------|---------------------|
| 1-28 | (an7) | 11 h | 94% | 78% |
| 1-29 | (an8) | 10 h | 91% | 50% |
| 1-30 | (an9) | 11 h | 81% | 59% |
| 1-31 | (an10) | 5 h | 88% | 78% |
| 1-32 | (an11) | 8 h | 90% | 68% |
| 1-33 | (an12) | 22 h | 74% | 66% |

4. Production of Spirolactone

Naphthol derivatives (na1) to (na4) shown below were used as a substrate (raw material) for producing a spirolactone. The reaction was monitored by thin-layer chromatography (TLC) using a TLC plate "Precoated TLC plate" (silica gel 60 GF254, 0.25 mm) manufactured by Merck.

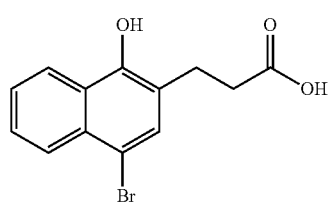

(na1)

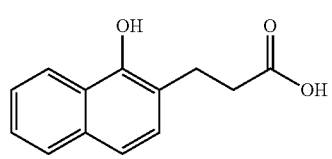

(na2)

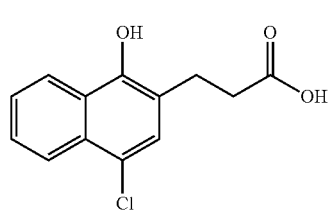

(na3)

-continued

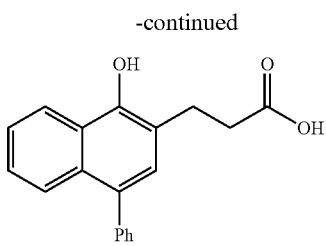
(na4)

Example 2-1

A reactor was charged with 216 mg (1 mmol) of 3-(1-hydroxynaphthalen-2-yl)propionic acid (na2), 36.9 mg (0.1 mmol) of tetrabutylammonium iodide ($Bu_4N^+I^-$), 0.21 mL of an aqueous solution containing 2 mmol of hydrogen peroxide as an oxidizing agent, and 5 mL of ethyl acetate as a solvent to prepare a solution. Hydrogen peroxide was used in an amount corresponding to 2 equivalents based on the substrate, and ethyl acetate was used in such an amount that the concentration of the substrate was 0.2 mol/L.

After adjusting the temperature of the reaction system to room temperature (about 20° C.), the mixture was reacted for 28 hours with stirring. After the addition of 5 mL of a sodium thiosulfate ($Na_2S_2O_3$) aqueous solution and 20 mL of a sodium hydrogen carbonate aqueous solution to the reaction mixture including the reaction product, the mixture was extracted twice with chloroform ($CHCl_3$). After the addition of excess anhydrous magnesium sulfate to the resulting organic layer, the solvent was evaporated under reduced pressure to obtain a crude product. The concentrate was subjected to silica gel flash column chromatography (eluant: hexane/ethyl acetate=10/1 to 4/1) to obtain (R)-1'H,3H-spiro(furan-2,2'-naphthalene)-1',5(4H)-dione (white solid) represented by the following formula (sb1). The yield was 28%. The analysis data for the resulting compound (sb1) is shown below.

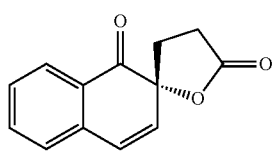
(sb1)

(R)-1'H,3H-Spiro[furan-2,2'-naphthalene]-1',5(4H)-dione

TLC (hexane:EtOAc:$CHCl_3$=1:2:1) $R_f$=0.46
$^1$H NMR ($CDCl_3$, 400 MHz) δ 2.18 (ddd, J=9.6, 11.0, 13.5 Hz, 1H), 2.49 (ddd, J=1.8, 9.6, 13.5 Hz, 1H), 2.60 (ddd, J=1.8, 9.6, 17.6 Hz, 1H), 2.92 (ddd, J=9.6, 11.0, 17.6 Hz, 1H), 6.21 (d, J=10.4 Hz, 1H), 6.66 (d, J=10.4 Hz, 1H), 7.26 (d, J=8.0 Hz, 1H), 7.41 (t, J=8.0 Hz, 1H), 7.62 (t, J=8.0 Hz, 1H), 8.02 (d, J=8.0 Hz, 1H)
$^{13}$C NMR ($CDCl_3$, 100 MHz) δ 26.5, 31.2, 83.4, 127.3, 127.8, 127.9, 127.9, 129.0, 132.3, 135.7, 136.8, 176.5, 196.5

Examples 2-2 to 2-19

A spirolactone was produced using 3-(4-bromo-1-hydroxynaphthalen-2-yl)propionic acid (na1), 3-(1-hydroxynaphthalen-2-yl)propionic acid (na2), 3-(4-chloro-1-hydroxynaphthalen-2-yl)propionic acid (na3), or 3-(4-phenyl-1-hydroxynaphthalen-2-yl)propionic acid (na4) as a substrate, and using a compound represented by the following general formula (25) wherein $R^5$ is 3,5-$(CF_3)_2C_6H_3$ or 3,5-(3,5-$(CF_3)_2$ $C_6H_3)_2C_6H_3$ as a quaternary ammonium salt, while changing type of the solvent and reaction conditions. The yield and the enantioselectivity are shown in Table 2-1.

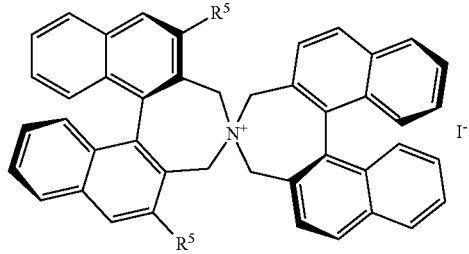
(25)

(R)-4'-Bromo-1'H,3H-spiro(furan-2,2'-naphthalene)-1',5(4H)-dione (white solid) represented by the following formula (sb2) was obtained in Examples 2-2 to 2-16. HPLC measurement for determining the enantioselectivity of (R)-4'-bromo-1'H,3H-spiro(furan-2,2'-naphthalene)-1',5(4H)-dione was performed using a chiral column "DAICEL CHIRALPAK OD-H" (eluant: hexane/isopropanol=85/15, flow rate: 1 mL/min) ($t_R$=18.8 min, $t_S$=22.3 min). The analysis data is shown below.

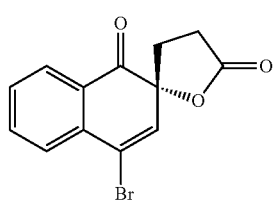
(sb2)

(R)-4'-Bromo-1'H,3H-spiro[furan-2,2'-naphthalene]-1',5(4H)-dione

TLC (hexane:EtOAc=1:1) $R_f$=0.43
IR (film) 3029, 1791, 1699, 1592, 1453, 1187 cm$^{-1}$
$^1$H NMR ($CDC_3$, 400 MHz) δ 2.24 (ddd, J=9.6, 11.0, 13.5 Hz, 1H), 2.46 (ddd, J=2.3, 9.6, 13.5 Hz, 1H), 2.62 (ddd, J=2.3, 9.6, 17.9 Hz, 1H), 2.90 (ddd, J=9.6, 11.0, 17.9 Hz, 1H), 6.67 (s, 1H), 7.49-7.53 (m, 1H), 7.73-7.78 (m, 2H), 8.05 (d, J=7.2 Hz, 1H)
$^{13}$C NMR ($CDCl_3$, 100 MHz) δ 26.5, 31.2, 84.2, 122.5, 127.0, 128.0, 128.8, 130.1, 133.4, 135.1, 135.9, 175.7, 194.7
HRMS (FAB+) m/z calcd for $C_{13}H_{10}BrO_3$ (M+H) 292.9813. found 292.9814 (R)-1'H,3H-Spiro(furan-2,2'-naphthalene)-1',5(4H)-dione represented by the formula (sb1) was obtained in Example 2-17.

(R)-4'-chlorospiro-1'H,3H-spiro(tetrahydrofuran-2,2'-(1'H-naphthalene)-1',5-dione (white solid) represented by the following formula (sb3) was obtained in Example 2-18. HPLC measurement for determining the enantioselectivity of (R)-4'-chlorospiro-1'H,3H-spiro(tetrahydrofuran-2,2'-(1'H-naphthalene)-1',5-dione was performed using a chiral column "DAICEL CHIRALPAK OD-H" (eluant: hexane/isopropanol=85/15, flow rate: 1 mL/min) ($t_R$=18.4 min, $t_S$=22.2 min). The analysis data is shown below.

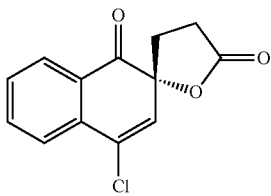

(sb3)

(R)-4'-Chlorospiro[tetrahydrofuran-2,2'-(1'H-naphthaline)]-1',5-dione

TLC (hexane:EtOAc=1:1) $R_f$=0.43
IR (film) 3018, 1788, 1700, 1595, 1454, 1293 cm$^{-1}$
$^1$H NMR (CDC$_3$, 400 MHz) δ 2.23 (ddd, J=9.6, 11.0, 13.4 Hz, 1H), 2.45 (ddd, J=2.3, 9.6, 13.4 Hz, 1H), 2.62 (ddd, J=2.3, 9.6, 17.9 Hz, 1H), 2.91 (ddd, J=9.6, 11.0, 17.9 Hz, 1H), 6.40 (s, 1H), 7.52 (dt, J=1.8, 7.4 Hz, 1H), 7.70-7.79 (m, 2H), 8.06 (d, J=7.4 Hz, 1H)
$^{13}$C NMR (CDCl$_3$, 100 MHz) δ 26.5, 31.5, 83.4, 126.1, 127.3, 128.1, 129.1, 130.1, 131.8, 134.5, 135.8, 175.7, 194.7
HRMS (FAB+) m/z calcd for C$_{13}$H$_{10}$ClO$_3$ (M+H) 249.0318. found 249.0316

(R)-4'-Phenyl-1'H,3H-spiro(furan-2,2'-naphthalene)-1',5 (4H)-dione (colorless crystal) represented by the following formula (sb4) was obtained in Example 2-19. HPLC measurement for determining the enantioselectivity of (R)-4'-Phenyl-1'H,3H-spiro(furan-2,2'-naphthalene)-1',5(4H)-dione was performed using a chiral column "DAICEL CHIRALPAK OD-H" (eluant: hexane/isopropanol=85/15, flow rate: 1 mL/min) ($t_R$=20.0 min, $t_S$=31.2 min). The analysis data is shown below.

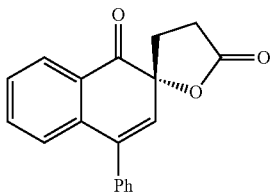

(sb4)

(R)-4'-Phenyl-1'H,3H-spiro[furan-2,2'-naphthalene]-1',5(4H)-dione

TLC (hexane:EtOAc=1:1) $R_f$=0.47
IR (film) 3027, 1783, 1687, 1593, 1280, 1176 cm$^{-1}$
$^1$H NMR (CDCl$_3$, 400 MHz) δ 2.27 (ddd, J=9.6, 11.0, 13.3 Hz, 1H), 2.54 (ddd, J=2.3, 9.6, 13.3 Hz, 1H), 2.63 (ddd, J=2.3, 9.6, 17.6 Hz, 1H), 2.93 (ddd, J=9.6, 11.0, 17.6 Hz, 1H), 6.12 (s, 1H), 7.15 (d, J=7.3 Hz, 1H), 7.34-7.50 (m, 6H), 7.56 (dt, J=1.4, 7.3 Hz, 1H), 8.10 (dd, J=1.4, 7.3 Hz, 1H)
$^{13}$C NMR (CDCl$_3$, 100 MHz) δ 26.7, 31.5, 83.7, 127.4, 127.6, 128.2, 128.4, 128.6 (2C), 128.7 (2C), 128.9, 130.6, 135.3, 137.4, 137.6, 139.8, 176.3, 196.4
HRMS (FAB+) m/z calcd for C$_{19}$H$_{15}$O$_3$ (M+H) 291.1021. found 291.1021

TABLE 2-1

| Example | Substrate | Quaternary ammonium salt | Solvent | Reaction tempereture, Time | Yield | Enantioselectivity |
|---|---|---|---|---|---|---|
| 2-2 | (na1) | General formula (25) | toluene/H$_2$O(1:1 v/v) | RT, 43 h | 26% | 53% |
| 2-3 | (na1) | R$^5$: 3,5-(CF$_3$)$_2$C$_6$H$_3$ | toluene/H$_2$O(1:2 v/v) | RT, 72 h | 45% | 52% |
| 2-4 | (na1) | General formula (25) | toluene/H$_2$O(5:1 v/v) | RT, 48 h | 68% | 51% |
| 2-5 | (na1) | R$^5$: 3,5-(3,5-(CF$_3$)$_2$C$_6$H$_3$)$_2$C$_6$H$_3$ | toluene/H$_2$O(2:1 v/v) | RT, 24 h | 48% | 88% |
| 2-6 | (na1) | | toluene/H$_2$O(1:1 v/v) | RT, 48 h | 48% | 82% |
| 2-7 | (na1) | | toluene/H$_2$O(1:2 v/v) | RT, 21 h | 44% | 80% |
| 2-8 | (na1) | | toluene/H$_2$O(1:1 v/v) | 50° C., 48 h | 50% | 51% |
| 2-9 | (na1) | | toluene/H$_2$O(1:1 v/v) | 10° C., 72 h | 47% | 84% |
| 2-10 | (na1) | | toluene/H$_2$O(2:1 v/v) | RT, 25 h | 27% | 90% |
| 2-11 | (na1) | | toluene/H$_2$O(2:1 v/v) | RT, 61 h | 55% | 82% |
| 2-12 | (na1) | | toluene/1M-brine(2:1 v/v) | RT, 25 h | 33% | 92% |
| 2-13 | (na1) | | toluene/H$_2$O(2:1 v/v) | 30° C., 24 h | 43% | 84% |
| 2-14 | (na1) | | toluene/1M-brine(2:1 v/v) | 30° C., 25 h | 45% | 86% |
| 2-15 | (na1) | | mesitylene/H$_2$O(2:1 v/v) | 30° C., 24 h | 31% | 90% |
| 2-16 | (na1) | | mesitylene/1M-brine(2:1 v/v) | 30° C., 24 h | 41% | 92% |
| 2-17 | (na2) | | toluene/1M-brine(2:1 v/v) | 30° C., 24 h | 14% | 55% |
| 2-18 | (na3) | | toluene/1M-brine(2:1 v/v) | 30° C., 24 h | 42% | 89% |
| 2-19 | (na4) | | toluene/1M-brine(2:1 v/v) | 30° C., 24 h | 95% | 84% |

5. Other (1)

The inventors also found that a spirolactone can be obtained from the naphthol derivative in high yield in a reaction system that includes a specific oxidizing agent without using a quaternary ammonium salt (outside the scope of the invention).

The specific oxidizing agent is preferably hydrogen peroxide, a urea-hydrogen peroxide adduct (UHP), tert-butyl hydroperoxide, or the like, and particularly preferably hydrogen peroxide. The amount of the oxidizing agent used is appropriately selected depending on the type of the substrate, but is normally in the range from 1 to 4 equivalents based on the substrate.

The components described above in connection with the spirolactone production conditions may be used as a solvent. The above description may be applied to the amount of the solvent.

The reaction temperature is appropriately selected depending on the type of the solvent and the like, but is preferably in the range from 0° C. to 100° C., and more preferably from 20° C. to 50° C., from the viewpoint of the reaction efficiency.

The atmosphere inside the reaction system may be air, inert gas, or the like.

After completion of the reaction, the product may optionally be subjected to a normal post-treatment (e.g., removal of the solvent, washing of the product, and chromatographic separation).

The above method can improve the yield of the spirolactone calculated based on the molar quantity of the substrate to 40% or higher. The yield can preferably be improved to 70% or higher (particularly preferably 80% or higher).

A production example of (R)-4'-bromo-1'H,3H-spiro(furan-2,2'-naphthalene)-1',5(4H)-dione (sb2) using 3-(1-hydroxynaphthalen-2-yl)propionic acid (na2) as a substrate is described below.

Reference Example 1

A reactor was charged with 216 mg (0.1 mmol) of 3-(1-hydroxynaphthalen-2-yl)propionic acid (na2), 0.21 mL of a 30% hydrogen peroxide aqueous solution containing 2 mmol of hydrogen peroxide as an oxidizing agent, and 5 mL of ethyl acetate as a solvent to prepare a solution. Hydrogen peroxide was used in an amount corresponding to 2 equivalents based on the substrate, and ethyl acetate was used in such an amount that the concentration of the substrate was 0.2 mol/L.

After adjusting the temperature of the reaction system to room temperature (about 20° C.), the mixture was reacted for 38 hours with stirring. After the addition of 20 mL of a sodium thiosulfate ($Na_2S_2O_3$) aqueous solution and 20 mL of a sodium hydrogen carbonate aqueous solution to the reaction mixture including the reaction product, the mixture was extracted twice with chloroform ($CHCl_3$). After the addition of excess anhydrous magnesium sulfate to the resulting organic layer, the solvent was evaporated under reduced pressure to obtain a crude product. The concentrate was subjected to silica gel flash column chromatography (eluant: hexane/ethyl acetate=11/1) to obtain (R)-4'-bromo-1'H,3H-spiro(furan-2,2'-naphthalene)-1',5(4H)-dione (sb2). The yield was 90%.

Reference Example 2

(R)-4'-Bromo-1'H,3H-spiro(furan-2,2'-naphthalene)-1',5(4H)-dione (sb2) was obtained in the same manner as in Reference Example 1, except that acetonitrile was used as a solvent instead of ethyl acetate, and the reaction time was changed to 19 hours. The yield was 80%.

Reference Example 3

(R)-4'-Bromo-1'H,3H-spiro(furan-2,2'-naphthalene)-1',5(4H)-dione (sb2) was obtained in the same manner as in Reference Example 1, except that toluene was used as a solvent instead of ethyl acetate, and the reaction time was changed to 19 hours. The yield was 50%.

6. Other (2)

The inventors succeeded in converting tert-butyl 2-(1-phenyl-1H-imidazole-2-carbonyl)indoline-1-carboxylate (as5) obtained in Example 1-20 into an ester (known compound) while maintaining the optical yield of the imidazole group (auxiliary group). The absolute configuration of the product was determined to be "S" referring to the literature value (see below).

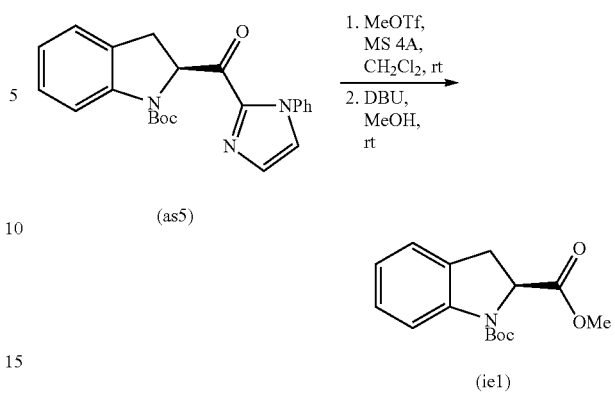

A reactor was charged with 24.4 mg (0.06 mmol) of tert-butyl 2-(1-phenyl-1H-imidazole-2-carbonyl)indoline-1-carboxylate (as5) (69% ee) obtained in Example 1-20, 50 mg of a molecular sieve (4 Å), and 1.2 mL of dichloromethane as a solvent. The mixture was reacted at room temperature for 30 minutes with stirring while adding 35 L (0.31 mmol) of methyl triflate (MeOTf), dropwise to the mixture. After confirming the absence of the raw material by TLC, the solvent and an excess reaction agent were evaporated under reduced pressure to obtain a concentrate including a crude product. After the addition of 1.2 mL of MeOH and 12 μL (0.08 mmol) of diazabicycloundecene (DBU), the mixture was stirred at room temperature for 11 hours. The reaction was then terminated by adding water to the reactor. The reaction product included in the reaction mixture was extracted with chloroform, and excess anhydrous sodium sulfate was added to the collected organic layer. The solvent was then evaporated under reduced pressure to obtain a concentrate including a crude product. The concentrate was subjected to silica gel flash column chromatography (eluant: hexane/ethyl acetate=1/1) to obtain 1-tert-butyl 2-methylindoline-1,2-dicarboxylate (colorless solid) represented by the formula (Ie) (yield: 78%). The enantioselectivity determined by HPLC measurement (chiral column: "DAICEL CHIRALPAK OD-H", eluant: hexane/isopropanol (=100/1), flow rate: 0.5 mL/min, $t_1$=27 min, $t_2$=37 min) was 69% ee. The analysis data for the resulting aniline derivative (ie) coincided with the literature value.

$[\alpha]^{22}_D$=−38.8 (c 0.94, $CHCl_3$) for 69% ee.

Literature value: $[\alpha]^{20}_D$=−57.7 (c 0.99, $CHCl_3$) for 78% ee (S configuration).

Literature: Kuwano et al., J. Am. Chem. Soc. 2000, 122, 7614.

INDUSTRIAL APPLICABILITY

A compound obtained by the production methods according to the invention may be suitable as a physiologically active substance, a drug, an agricultural chemical, a cosmetic preparation, or the like.

The invention claimed is:

1. A method for producing a compound represented by the formula (22):

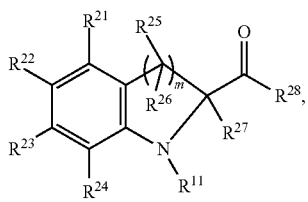

(22)

comprising reacting a compound represented by formula (21) with a quaternary ammonium salt represented by formula (1):

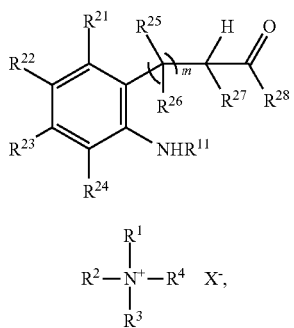

(21)

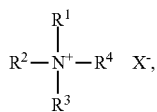

(1)

and an oxidizing agent,
wherein
X is an iodine atom;
$R^1$, $R^2$, $R^3$ and $R^4$ are independently a hydrocarbon group having 1 to 30 carbon atoms in which some hydrogen atoms are optionally replaced with a halogen atom, provided that $R^1$ and $R^2$ are optionally bonded to each other to form a divalent organic group that is bonded to the nitrogen atom,
wherein $R^3$ and $R^4$ are optionally bonded to each other to form a divalent organic group that is bonded to the nitrogen atom;
$R^{11}$ is a hydrogen atom, a tert-butoxycarbonyl group, a benzyloxycarbonyl group, a 2,2,2-trichloroethoxycarbonyl group, or a methanesulfonyl group;
$R^{21}$, $R^{22}$, $R^{23}$ and $R^{24}$ are independently a hydrogen atom, a halogen atom, an alkoxy group having 1 to 10 carbon atoms, or a linear, branched or cyclic hydrocarbon group having 1 to 20 carbon atoms in which some hydrogen atoms are optionally replaced with a halogen atom,
wherein one, two or all of the combinations of $R^{21}$ and $R^{22}$, $R^{22}$ and $R^{23}$, and $R^{23}$ and $R^{24}$ are optionally bonded to each other to form a divalent organic group;
$R^{25}$ and $R^{26}$ are independently a hydrogen atom or a linear, branched or cyclic hydrocarbon group having 1 to 20 carbon atoms in which some hydrogen atoms are optionally replaced with a halogen atom;
$R^{27}$ is a hydrogen atom or a linear, branched or cyclic hydrocarbon group having 1 to 20 carbon atoms in which some hydrogen atoms are optionally replaced with a halogen atom;
$R^{28}$ is a heteroaryl group having 3 to 20 carbon atoms or a linear, branched or cyclic hydrocarbon group having 1 to 20 carbon atoms in which some hydrogen atoms are optionally replaced with a halogen atom; and
m is 1 or 2.

2. The method according to claim 1, wherein the quaternary ammonium salt is an N-spiro quaternary ammonium salt represented by formula (2):

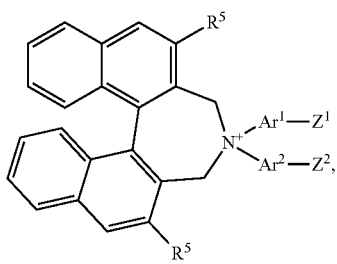

(2)

wherein $R^5$ is selected from the group consisting of
a hydrogen atom,
a linear, branched or cyclic alkyl group having 1 to 6 carbon atoms in which some hydrogen atoms are optionally replaced with a halogen atom,
a linear, branched or cyclic alkenyl group having 2 to 6 carbon atoms in which some hydrogen atoms are optionally replaced with a halogen atom,
a linear, branched or cyclic alkynyl group having 2 to 6 carbon atoms in which some hydrogen atoms are optionally replaced with a halogen atom,
an aralkyl group in which some hydrogen atoms are optionally replaced with an alkyl group having 1 to 4 carbon atoms in which some hydrogen atoms are optionally replaced with a halogen atom, an alkoxy group having 1 to 3 carbon atoms in which some hydrogen atoms are optionally replaced with a halogen atom, or a halogen atom,
a heteroaralkyl group in which some hydrogen atoms are optionally replaced with an alkyl group having 1 to 4 carbon atoms in which some hydrogen atoms are optionally replaced with a halogen atom, an alkoxy group having 1 to 3 carbon atoms in which some hydrogen atoms are optionally replaced with a halogen atom, or a halogen atom,
an aryl group in which some hydrogen atoms are optionally replaced with an alkyl group having 1 to 4 carbon atoms in which some hydrogen atoms are optionally replaced with a halogen atom, an alkoxy group having 1 to 3 carbon atoms in which some hydrogen atoms are optionally replaced with a halogen atom, or a halogen atom,
an aryl group in which some hydrogen atoms are optional replaced with an aryl group that is optionally substituted with an alkyl group having 1 to 4 carbon atoms in which some hydrogen atoms are optionally replaced with a halogen atom,
a heteroaryl group in which some hydrogen atoms are optionally replaced with an alkyl group having 1 to 4 carbon atoms in which some hydrogen atoms are optionally replaced with a halogen atom,
an alkoxy group having 1 to 3 carbon atoms in which some hydrogen atoms are optionally replaced with a halogen atom,
a ($C_{1-3}$ alkoxy)carbonyl group, an N—($C_{1-4}$ alkyl)carbonyl group, a carbamoyl group, an N—($C_{1-4}$ alkyl)carbamoyl group, and an N,N-di($C_{1-4}$ alkyl)carbamoyl group wherein the $C_{1-4}$ alkyl groups are identical or different;

$Ar^1$ and $Ar^2$ are independently a divalent group selected from the group consisting of an aryl group in which some hydrogen atoms are optionally replaced with a halogen atom, an alkyl group having 2 to 5 carbon atoms, an alkoxy group having 2 to 4 carbon atoms, an alkenyl group having 3 to 7 carbon atoms, an alkynyl group having 3 to 7 carbon atoms, an aryl group in which some hydrogen atoms are optionally replaced with an alkyl group having 1 to 6 carbon atoms, an alkoxy group having 1 to 6 carbon atoms, or a halogen atom, an aryl group in which some hydrogen atoms are substituted with an aryl group in which some hydrogen atoms are optionally replaced with an alkyl group having 1 to 6 carbon atoms, an alkoxy group having 1 to 6 carbon atoms, or a halogen atom, an aryl group in which some hydrogen atoms are optional replaced with a heteroaryl group in which some hydrogen atoms are optionally replaced with an alkyl group having 1 to 6 carbon atoms, an alkoxy group having 1 to 6 carbon atoms, or a halogen atom, a heteroaryl group in which some hydrogen atoms are optionally replaced with an alkyl group having 1 to 6 carbon atoms, an alkoxy group having 1 to 6 carbon atoms, or a halogen atom, a heteroaryl group in which some hydrogen atoms are optional replaced with an aryl group in which some hydrogen atoms are optionally replaced with an alkyl group having 1 to 6 carbon atoms, an alkoxy group having 1 to 6 carbon atoms, or a halogen atom, a heteroaryl group in which some hydrogen atoms are optionally replaced with a heteroaryl group in which some hydrogen atoms are optionally replaced with an alkyl group having 1 to 6 carbon atoms, an alkoxy group having 1 to 6 carbon atoms, or a halogen atom, and a heteroaryl group in which some hydrogen atoms are optionally replaced with an alkyl group having 1 to 4 carbon atoms, an alkoxy group having 1 to 3 carbon atoms, or a halogen atom; and $Z^1$ and $Z^2$ are independently selected from the group consisting of a hydrogen atom, a halogen atom, an alkyl group having 1 to 4 carbon atoms, and an alkoxy group having 1 to 3 carbon atoms, wherein $Z^1$ and $Z^2$ are optionally bonded to each other to form a single bond or a divalent hydrocarbon group.

3. The method of claim 1, wherein the oxidizing agent comprises at least one member selected from the group consisting of hydrogen peroxide, a urea-hydrogen peroxide adduct (UHP), tert-butyl hydroperoxide, di-tert-butyl peroxide, tert-amyl hydroperoxide, di-tert-amyl peroxide, cumene hydroperoxide, dicumyl peroxide, tert-butylcumyl peroxide, tert-butyl peroxypivalate, benzoyl peroxide, lauroyl peroxide, ethylbenzene hydroperoxide, peracetic acid and perbenzoic acid.

4. The method of claim 1, wherein the quaternary ammonium salt is represented by formula (25):

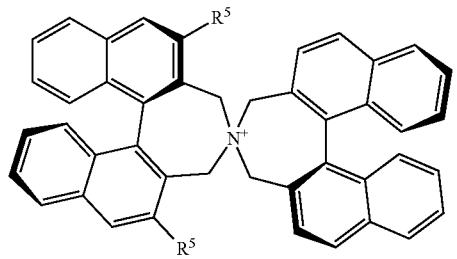

(25)

wherein $R^5$ is 3,5-(3,5-$(CF_3)_2C_6H_3)_2C_6H_3$ or 4-(4-$CF_3C_6H_4)C_6H_4$.

5. A method of for producing a compound represented by the formula (43):

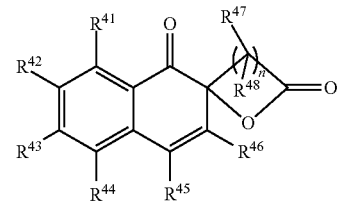

(43)

comprising reacting a compound represented by formula (41) with a quaternary ammonium salt represented by formula (1):

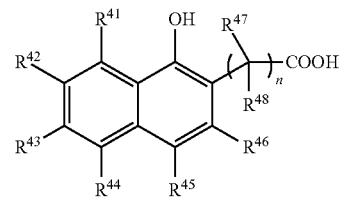

(41)

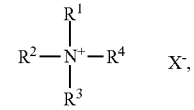

(1)

and an oxidizing agent,
wherein
X is an iodine atom;
$R^1$, $R^2$, $R^3$ and $R^4$ are independently a hydrocarbon group having 1 to 30 carbon atoms in which some hydrogen atoms are optionally replaced with a halogen atom, wherein $R^1$ and $R^2$ are optionally bonded to each other to form a divalent organic group that is bonded to the nitrogen atom, and $R^3$ and $R^4$ are optionally bonded to each other to form a divalent organic group that is bonded to the nitrogen atom;
$R^{41}$, $R^{42}$, $R^{43}$, $R^{44}$, $R^{45}$ and $R^{46}$ are independently a hydrogen atom, a halogen atom, an alkoxy group having 1 to 10 carbon atoms, or a linear, branched or cyclic hydrocarbon group having 1 to 20 carbon atoms in which some hydrogen atoms are optionally replaced with a halogen atom, provided that one, two, three, four or all of the combinations of $R^{41}$ and $R^{42}$, $R^{42}$ and $R^{43}$, $R^{43}$ and $R^{44}$, $R^{44}$ and $R^{45}$, and $R^{45}$ and $R^{46}$ are optionally bonded to each other to form a divalent organic group;

$R^{47}$ and $R^{48}$ are independently a hydrogen atom or a linear, branched or cyclic hydrocarbon group having 1 to 20 carbon atoms in which some hydrogen atoms are optionally replaced with a halogen atom; and n is 2 or 3.

6. The method of claim 5, wherein the quaternary ammonium salt is an N-spiro quaternary ammonium salt represented by formula (2):

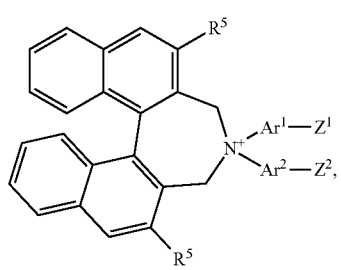

(2)

wherein $R^5$ is selected from the group consisting of a hydrogen atom, a linear, branched or cyclic alkyl group having 1 to 6 carbon atoms in which some hydrogen atoms are optionally replaced with a halogen atom, a linear, branched or cyclic alkenyl group having 2 to 6 carbon atoms in which some hydrogen atoms are optionally replaced with a halogen atom, a linear, branched or cyclic alkynyl group having 2 to 6 carbon atoms in which some hydrogen atoms are optionally replaced with a halogen atom, an aralkyl group in which some hydrogen atoms are optionally replaced with an alkyl group having 1 to 4 carbon atoms in which some hydrogen atoms are optionally replaced with a halogen atom, an alkoxy group having 1 to 3 carbon atoms in which some hydrogen atoms are optionally replaced with a halogen atom, or a halogen atom, a heteroaralkyl group in which some hydrogen atoms are optionally replaced with an alkyl group having 1 to 4 carbon atoms in which some hydrogen atoms are optionally replaced with a halogen atom, an alkoxy group having 1 to 3 carbon atoms in which some hydrogen atoms are optionally replaced with a halogen atom, or a halogen atom, an aryl group in which some hydrogen atoms are optionally replaced with an alkyl group having 1 to 4 carbon atoms in which some hydrogen atoms are optionally replaced with a halogen atom, an alkoxy group having 1 to 3 carbon atoms in which some hydrogen atoms are optionally replaced with a halogen atom, or a halogen atom, an aryl group in which some hydrogen atoms are optional replaced with an aryl group that is optionally substituted with an alkyl group having 1 to 4 carbon atoms in which some hydrogen atoms are optionally replaced with a halogen atom, a heteroaryl group in which some hydrogen atoms are optionally replaced with an alkyl group having 1 to 4 carbon atoms in which some hydrogen atoms are optionally replaced with a halogen atom, an alkoxy group having 1 to 3 carbon atoms in which some hydrogen atoms are optionally replaced with a halogen atom, or a halogen atom, a ($C_{1-3}$ alkoxy)carbonyl group, an N—($C_{1-4}$ alkyl)carbonyl group, a carbamoyl group, an N—($C_{1-4}$ alkyl)carbamoyl group, and an N,N-di($C_{1-4}$ alkyl)carbamoyl group wherein the $C_{1-4}$ alkyl groups are identical or different;

$Ar^1$ and $Ar^2$ are independently a divalent group selected from the group consisting of an aryl group in which some hydrogen atoms are optionally replaced with a halogen atom, an alkyl group having 2 to 5 carbon atoms, an alkoxy group having 2 to 4 carbon atoms, an alkenyl group having 3 to 7 carbon atoms, an alkynyl group having 3 to 7 carbon atoms, an aryl group in which some hydrogen atoms are optionally replaced with an alkyl group having 1 to 6 carbon atoms, an alkoxy group having 1 to 6 carbon atoms, or a halogen atom, an aryl group in which some hydrogen atoms are optional replaced with an aryl group in which some hydrogen atoms are optionally replaced with an alkyl group having 1 to 6 carbon atoms, an alkoxy group having 1 to 6 carbon atoms, or a halogen atom, an aryl group in which some hydrogen atoms are optional replaced with a heteroaryl group in which some hydrogen atoms are optionally replaced with an alkyl group having 1 to 6 carbon atoms, an alkoxy group having 1 to 6 carbon atoms, or a halogen atom, a heteroaryl group in which some hydrogen atoms are optionally replaced with an alkyl group having 1 to 6 carbon atoms, an alkoxy group having 1 to 6 carbon atoms, or a halogen atom, a heteroaryl group in which some hydrogen atoms are optional replaced with an aryl group in which some hydrogen atoms are optionally replaced with an alkyl group having 1 to 6 carbon atoms, an alkoxy group having 1 to 6 carbon atoms, or a halogen atom, a heteroaryl group in which some hydrogen atoms are optionally replaced with a heteroaryl group in which some hydrogen atoms are optionally replaced with an alkyl group having 1 to 6 carbon atoms, an alkoxy group having 1 to 6 carbon atoms, or a halogen atom, and a heteroaryl group in which some hydrogen atoms are optionally replaced with an alkyl group having 1 to 4 carbon atoms, an alkoxy group having 1 to 3 carbon atoms, or a halogen atom; and $Z^1$ and $Z^2$ are independently a group selected from the group consisting of a hydrogen atom, a halogen atom, an alkyl group having 1 to 4 carbon atoms, and an alkoxy group having 1 to 3 carbon atoms, wherein $Z^1$ and $Z^2$ are optionally bonded to each other to form a single bond or a divalent hydrocarbon group.

7. The method of claim 5, wherein the oxidizing agent comprises at least one member selected from the group consisting of hydrogen peroxide, a urea-hydrogen peroxide adduct (UHP), tert-butyl hydroperoxide, di-tert-butyl peroxide, tert-amyl hydroperoxide, di-tert-amyl peroxide, cumene hydroperoxide, dicumyl peroxide, tert-butylcumyl peroxide, tert-butyl peroxypivalate, benzoyl peroxide, lauroyl peroxide, ethylbenzene hydroperoxide, peracetic acid and perbenzoic acid.

8. The method of claim 5, wherein the quaternary ammonium salt is represented by formula (25):

(25)

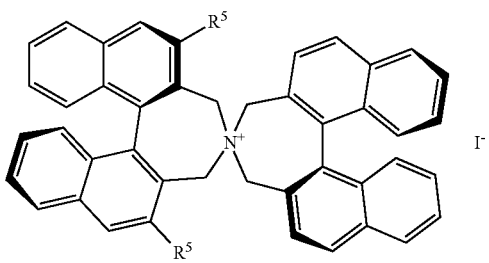

wherein $R^5$ is 3,5-$(3,5-(CF_3)_2C_6H_3)_2C_6H_3$ or 4-(4-$CF_3C_6H_4)C_6H_4$.

9. A method for producing a compound represented by the formula (44):

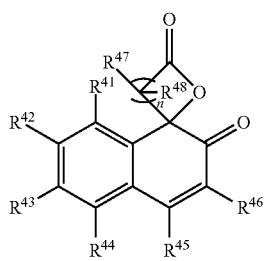

(44)

comprising reacting a compound represented by formula (42) with a quaternary ammonium salt represented by formula (1):

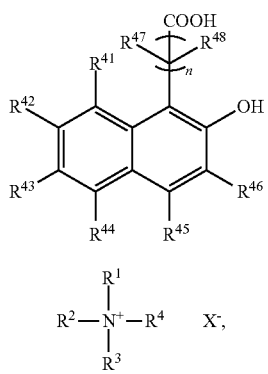

(42)

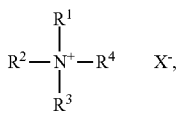

(1)

and an oxidizing agent,
wherein
X is an iodine atom;
$R^1$, $R^2$, $R^3$ and $R^4$ are independently a hydrocarbon group having 1 to 30 carbon atoms in which some hydrogen atoms are optionally replaced with a halogen atom,
wherein $R^1$ and $R^2$ are optionally bonded to each other to form a divalent organic group that is bonded to the nitrogen atom, and $R^3$ and $R^4$ are optionally bonded to each other to form a divalent organic group that is bonded to the nitrogen atom;
$R^{41}$, $R^{42}$, $R^{43}$, $R^{44}$, $R^{45}$ and $R^{46}$ are independently a hydrogen atom, a halogen atom, an alkoxy group having 1 to 10 carbon atoms, or a linear, branched or cyclic hydrocarbon group having 1 to 20 carbon atoms in which some hydrogen atoms are optionally replaced with a halogen atom,
wherein one, two, three, four or all of the combinations of $R^{41}$ and $R^{42}$, $R^{42}$ and $R^{43}$, $R^{43}$ and $R^{44}$, $R^{44}$ and $R^{45}$, and $R^{45}$ and $R^{46}$ are optionally bonded to each other to form a divalent organic group;
$R^{47}$ and $R^{48}$ are independently a hydrogen atom or a linear, branched or cyclic hydrocarbon group having 1 to 20 carbon atoms in which some hydrogen atoms are optionally replaced with a halogen atom; and
n is 2 or 3.

10. The method of claim 9, wherein the quaternary ammonium salt is an N-Spiro quaternary ammonium salt represented by formula (2):

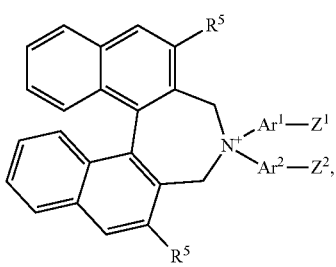

(2)

wherein $R^5$ is selected from the group consisting of
a hydrogen atom,
a linear, branched or cyclic alkyl group having 1 to 6 carbon atoms in which some hydrogen atoms are optionally replaced with a halogen atom,
a linear, branched or cyclic alkenyl group having 2 to 6 carbon atoms in which some hydrogen atoms are optionally replaced with a halogen atom,
a linear, branched or cyclic alkynyl group having 2 to 6 carbon atoms in which some hydrogen atoms are optionally replaced with a halogen atom,
an aralkyl group in which some hydrogen atoms are optionally replaced with an alkyl group having 1 to 4 carbon atoms in which some hydrogen atoms are optionally replaced with a halogen atom, an alkoxy group having 1 to 3 carbon atoms in which some hydrogen atoms are optionally replaced with a halogen atom, or a halogen atom,
a heteroaralkyl group in which some hydrogen atoms are optionally replaced with an alkyl group having 1 to 4 carbon atoms in which some hydrogen atoms are optionally replaced with a halogen atom, an alkoxy group having 1 to 3 carbon atoms in which some hydrogen atoms are optionally replaced with a halogen atom, or a halogen atom,
an aryl group in which some hydrogen atoms are optionally replaced with an alkyl group having 1 to 4 carbon atoms in which some hydrogen atoms are optionally replaced with a halogen atom, an alkoxy group having 1 to 3 carbon atoms in which some hydrogen atoms are optionally replaced with a halogen atom, or a halogen atom,
an aryl group in which some hydrogen atoms are optional replaced with an aryl group that is optionally substituted with an alkyl group having 1 to 4 carbon atoms in which some hydrogen atoms are optionally replaced with a halogen atom,
a heteroaryl group in which some hydrogen atoms are optionally replaced with an alkyl group having 1 to 4 carbon atoms in which some hydrogen atoms are optionally replaced with a halogen atom, an alkoxy group having 1 to 3 carbon atoms in which some hydrogen atoms are optionally replaced with a halogen atom, or a halogen atom, a ($C_{1-3}$ alkoxy)carbonyl group, an N—($C_{1-4}$ alkyl)carbonyl group, a carbamoyl group, an N—($C_{1-4}$ alkyl)carbamoyl group, and an N,N-di($C_{1-4}$ alkyl)carbamoyl group wherein the $C_{1-4}$ alkyl groups are identical or different;

$Ar^1$ and $Ar^2$ are independently a divalent group selected from the group consisting of an aryl group in which some hydrogen atoms are optionally replaced with a halogen atom, an alkyl group having 2 to 5 carbon atoms, an alkoxy group having 2 to 4 carbon atoms, an alkenyl group having 3 to 7 carbon atoms, an alkynyl group having 3 to 7 carbon atoms, an aryl group in which some hydrogen atoms are optionally replaced with an alkyl group having 1 to 6 carbon atoms, an alkoxy group having 1 to 6 carbon atoms, or a halogen atom, an aryl group in which some hydrogen atoms are optional replaced with an aryl group in which some hydrogen atoms are optionally replaced with an alkyl group having 1 to 6 carbon atoms, an alkoxy group having 1 to 6 carbon atoms, or a halogen atom, an aryl group in which some hydrogen atoms are substituted with a heteroaryl group in which some hydrogen atoms are optionally replaced with an alkyl group having 1 to 6 carbon atoms, an alkoxy group having 1 to 6 carbon atoms, or a halogen atom, a heteroaryl group in which some hydrogen atoms are optionally replaced with an alkyl group having 1 to 6 carbon atoms, an alkoxy group having 1 to 6 carbon atoms, or a halogen atom, a heteroaryl group in which some hydrogen atoms are optional replaced with an aryl group in which some hydrogen atoms are optionally replaced with an alkyl group having 1 to 6 carbon atoms, an alkoxy group having 1 to 6 carbon atoms, or a halogen atom, a heteroaryl group in which some hydrogen atoms are optionally replaced with a heteroaryl group in which some hydrogen atoms are optionally replaced with an alkyl group having 1 to 6 carbon atoms, an alkoxy group having 1 to 6 carbon atoms, or a halogen atom, and a heteroaryl group in which some hydrogen atoms are optionally replaced with an alkyl group having 1 to 4 carbon atoms, an alkoxy group having 1 to 3 carbon atoms, or a halogen atom; and $Z^1$ and $Z^2$ are independently a group selected from the group consisting of a hydrogen atom, a halogen atom, an alkyl group having 1 to 4 carbon atoms, and an alkoxy group having 1 to 3 carbon atoms, wherein $Z^1$ and $Z^2$ are optionally bonded to each other to form a single bond or a divalent hydrocarbon group.

11. The method of claim 9, wherein the oxidizing agent comprises at least one member selected from the group consisting of hydrogen peroxide, a urea-hydrogen peroxide adduct (UHP), tert-butyl hydroperoxide, di-tert-butyl peroxide, tert-amyl hydroperoxide, di-tert-amyl peroxide, cumene hydroperoxide, dicumyl peroxide, tert-butylcumyl peroxide, tert-butyl peroxypivalate, benzoyl peroxide, lauroyl peroxide, ethylbenzene hydroperoxide, peracetic acid and perbenzoic acid.

12. The method of claim 9, wherein the quaternary ammonium salt is represented by formula (25):

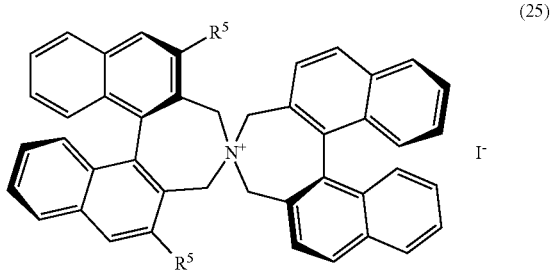

(25)

wherein $R^5$ is 3,5-(3,5-$(CF_3)_2C_6H_3)_2C_6H_3$ or 4-(4-$CF_3C_6H_4)C_6H_4$.

* * * * *